US 12,089,884 B2

(12) United States Patent
Schlatterer

(10) Patent No.: US 12,089,884 B2
(45) Date of Patent: Sep. 17, 2024

(54) PERIPROSTHETIC HIP FRACTURE CABLING SYSTEM

(71) Applicant: Daniel Robert Schlatterer, Dunwoody, GA (US)

(72) Inventor: Daniel Robert Schlatterer, Dunwoody, GA (US)

( * ) Notice: Subject to any disclaimer, the term of this patent is extended or adjusted under 35 U.S.C. 154(b) by 112 days.

(21) Appl. No.: 17/692,556

(22) Filed: Mar. 11, 2022

(65) Prior Publication Data

US 2022/0338911 A1     Oct. 27, 2022

Related U.S. Application Data

(60) Provisional application No. 63/177,479, filed on Apr. 21, 2021.

(51) Int. Cl.
    *A61B 17/82*     (2006.01)
    *A61B 17/68*     (2006.01)

(52) U.S. Cl.
    CPC ........ *A61B 17/82* (2013.01); *A61B 2017/681* (2013.01)

(58) Field of Classification Search
    CPC . A61B 17/8872; A61B 17/82; A61B 17/8028; A61B 2017/0406; A61B 17/842
    See application file for complete search history.

(56) References Cited

U.S. PATENT DOCUMENTS

| | | | |
|---|---|---|---|
| 3,469,573 A | 9/1969 | Florio | |
| 4,667,662 A | 5/1987 | Titone | |
| 5,611,801 A | 3/1997 | Songer | |
| 5,665,089 A * | 9/1997 | Dall | A61B 17/80 606/908 |
| 5,993,452 A * | 11/1999 | Vandewalle | A61B 17/82 606/103 |
| 6,475,220 B1 | 11/2002 | Whiteside | |
| 6,589,246 B1 | 7/2003 | Hack et al. | |
| 9,333,021 B2 * | 5/2016 | Gephart | A61B 17/8076 |
| 9,387,024 B2 | 7/2016 | Schlatterer | |
| 10,835,301 B1 * | 11/2020 | Paranjpe | A61B 17/809 |
| 10,952,781 B2 | 3/2021 | Kobayashi | |

(Continued)

FOREIGN PATENT DOCUMENTS

| | | |
|---|---|---|
| CN | 201631354 | 11/2010 |
| CN | 202161448 | 3/2012 |

(Continued)

*Primary Examiner* — David W Bates
(74) *Attorney, Agent, or Firm* — David O. Simmons

(57) ABSTRACT

An improved fracture cabling system has one or more spacers. Each spacer has a longitudinal length extending along a body of the spacer. The body has an upper portion with an aperture configured to receive a wire or cable and a lower portion having one or more pairs of feet spaced by a longitudinal gap or groove. Each of the one or more pairs of feet is located on a lateral side of the spacer body and configured to contact a bone with a fracture. The gap is configured to be positioned over the fracture with each foot positioned on a side of the bone spaced from the fracture. The longitudinal length of the one or more spacers is preferably curved or arcuate. Each body of the one or more spacers has a leading end and a trailing end.

30 Claims, 20 Drawing Sheets
(4 of 20 Drawing Sheet(s) Filed in Color)

(56) References Cited

U.S. PATENT DOCUMENTS

| | | | |
|---|---|---|---|
| 2003/0093091 A1* | 5/2003 | Paolitto | A61B 17/12009 606/139 |
| 2005/0171547 A1* | 8/2005 | Aram | A61B 17/8861 606/74 |
| 2005/0177162 A1* | 8/2005 | McLeod | A61B 17/8028 606/301 |
| 2012/0059417 A1* | 3/2012 | Norton | A61B 17/0401 606/232 |
| 2012/0272816 A1 | 11/2012 | Ueda et al. | |
| 2013/0289564 A1* | 10/2013 | Bernstein | A61B 17/82 606/74 |
| 2014/0243901 A1* | 8/2014 | Mebarak | A61B 17/808 606/280 |
| 2018/0161083 A1* | 6/2018 | Kobayashi | A61B 17/809 |
| 2021/0307799 A1* | 10/2021 | Del Medico | A61B 17/809 |

FOREIGN PATENT DOCUMENTS

| | | |
|---|---|---|
| JP | 2011110365 | 6/2011 |
| WO | 2020070596 | 4/2020 |

* cited by examiner

PERIPROSTHETIC HIP FRACTURE CABLING SYSTEM

TECHNICAL FIELD

The present invention relates to an improved bone binding device for the cerclage of fractured bones and bone stabilization and reinforcement, generally. The present invention further relates to an improved binding for securing and immobilizing long bone fractures, periprosthetic fractures, osteotomies, or other bony instability instances. One such application would be for fractures or orthopedic adult reconstructive procedures, revision hip or knee procedures, and so forth in osteoporotic bone.

BACKGROUND OF THE INVENTION

The annual rate of total hip replacement procedures increases as our population ages. Hip replacement surgeries are highly successful in alleviating hip pain and improving patients' functional capabilities. One pitfall of hip replacement surgery is that the hip stem in the upper half of the femur shields weight bearing on the surrounding bone. This results in a gradual decrease in bone density and bone strength in direct response to less loading on the bone. Moreover, hip replacement patients have ongoing bone strength loss or osteoporosis due to their continual aging process. Taken together, hip replacement patients have weaker bone and are at high risk for periprosthetic hip fractures (PPHF). These fractures are challenging to repair and often fail repair procedures. One reason for repair failure is the presence of the hip stem, which again complicates matters. The hip stem complicates the PPHF because the metal hip stem blocks passage of bone screws from one femoral cortex through the medullary canal and out the opposite femoral cortex for fracture repair.

One method of PPHF repair is applying cables or cerclage circumferentially around the fractured femur for repair. The decreased femoral bone density again comes into play because the thin cables are typically 2 mm or less in diameter and easily penetrate the weakened bone and either cause secondary fractures or the cable has insufficient fixation to hold the PPHF together until union. Some surgeons will place cortical allografts over the femur and under the cables to improve fracture repair construct strength. The cortical allograft fracture fixation with cables has variable success, and it is costly with an associated disease transmission risk.

In the repair of bone fractures, the use of cerclage wires is known. The cerclage wires apply a circumferential compression force to the bone portion by tensioning the cerclage wire tightened against the bone and locked or clamped. An issue of bone damage can occur due to the narrow width of the wire diameter which can cut off blood flow to the bone. This can result in the risk of bone tissue necrosis due to contact with the cerclage wires.

Several attempts to resolve this issue have been developed as found in WO 2020/070596 A1 patent application entitled "Device For The Cerclage Of Fractured Bones And System For The Cerclage Of Fractured Bones Comprising Such Device". This band spacer effectively lies flat against the bone being repaired.

In U.S. Pat. No. 5,993,452 entitled "Cerclage System", a similar cerclage system is taught. The patent employs resorbable bands with a second resorbable member or spacer which supports the band in a spaced relationship. This second member in a preferred embodiment is a plurality of spacers of a rectangular shape with a flat bone contacting surface to spread the compressive forces applied to the bone.

In U.S. Pat. No. 10,952,781 B2 entitled "Cable Saddle", the use of a plurality of cable links allows the cable wire to tension the plurality of links and to tension the wire while the compressive forces of the cable links spread across the bone. Like the previously noted prior art, the cable links have a bone contacting surface that extends across the transverse width of the cable links, effectively creating a flat, albeit with ridges, load bearing surface against the bone.

The present invention provides an improved cerclage system that distributes the bone compressive loads at spaced locations circumferentially along the longitudinal length of the cable or wire as well as at space locations laterally relative to the width thereby avoiding a flat bone contacting surface, but still reducing the contact pressure compared to the cerclage wire alone.

The current invention, by comparison to the prior art, improves the fixation properties of cables in use currently. It decreases the cortical penetration of current cables by the cable passage through a hollow device herein called weak bone binder [WBB] having an increased surface area via multiple feet, which distribute the cable tension more widely on the femur. The present device differs from the limited contact cabling system previously patented by Daniel Schlatterer in U.S. Pat. No. 9,387,024 B2 issued Jul. 12, 2016. A primary difference is the provision of cable spacer feet, sized up to 3 mm each or greater. This has found in benchtop studies to enhance cable fixation and decrease cable cortical penetration.

This system and device are further described hereinafter and provides a way to more safely repair bone fractures, but also to stabilize the femur when repairing a hip to avoid fractures.

SUMMARY OF THE INVENTION

An improved fracture cabling system has one or more spacers. Each spacer has a longitudinal length extending along a body of the spacer. The body has an upper portion with an aperture configured to receive a wire or cable and a lower portion having one or more pairs of feet spaced by a longitudinal gap or groove. Each of the one or more pairs of feet is located on a lateral side of the spacer body and configured to contact a bone with a fracture. The gap is configured to be positioned over the fracture with each foot positioned on a side of the bone spaced from the fracture. The longitudinal length of the one or more spacers is preferably curved or arcuate. Each body of the one or more spacers has a leading end and a trailing end. The cabling system can also be used as a fracture minimizing cabling system that is particularly useful in osteoporotic bone.

In one embodiment, the improved fracture binding has a plurality of spacers. Each spacer abuts an adjacent spacer at the leading end or the trailing end. Each spacer has a leading end and a trailing end spaced arcuately between 15 degrees to 180 degrees or between 90 degrees and 180 degrees.

The one or more spacers have a pair of sides. Each side has the pairs of feet configured to engage the bone at longitudinally spaced locations. The feet at the leading or trailing ends are partially rounded in shape, and the pairs of feet located from the ends are rounded in shape. The fracture cabling system has a cable. The cable is inserted through the aperture of each of the one or more spacers and when tightened, secures each spacer in contact with the bone securely to set the fracture.

The invention further includes an improved bone stabilizing cabling system that has one or more spacers. Each spacer has a longitudinal length extending along a body of the spacer, the body having an upper portion with an aperture configured to receive a wire or cable and a lower portion having one or more pairs of feet spaced by a longitudinal gap or groove. Each of the one or more pairs of feet is located on a lateral side of the spacer body and configured to contact a bone in near proximity to a femoral head of the bone. The gap is configured to be positioned over the bone with each foot positioned on a side of the bone spaced from the femoral head to stabilize and reinforce the bone.

The longitudinal length of the one or more spacers is curved or arcuate. Each body of the one or more spacers has a leading end and a trailing end. Preferably, the improved bone stabilizing cabling system has a plurality of spacers. Each spacer abuts an adjacent spacer at the leading end or trailing end. Each spacer has a leading end and a trailing end spaced arcuately between 15 degrees to 180 degrees, alternatively between 90 degrees and 180 degrees.

The one or more spacers have a pair of sides. Each side has the pairs of feet configured to engage the bone at longitudinally spaced locations. The feet at the leading or trailing ends are partially rounded in shape and the pairs of feet located from the ends are rounded in shape. The improved bone stabilizing cabling system further has a cable. The cable is inserted through the aperture of each of the one or more spacers and when tightened, secures each spacer in contact with the bone securely to reinforce the bone. The feet of the one or more spacers can have a width wider than the cable passed through the spacer increasing the contact area of the spacer such that penetration of the spacer and or cortical compromise by the spacer is prevented and a more stable periprosthetic fracture fixation construct is achieved.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will be described by way of example and with reference to the accompanying drawings in which.

DETAILED DESCRIPTION OF THE INVENTION

Figure 16:
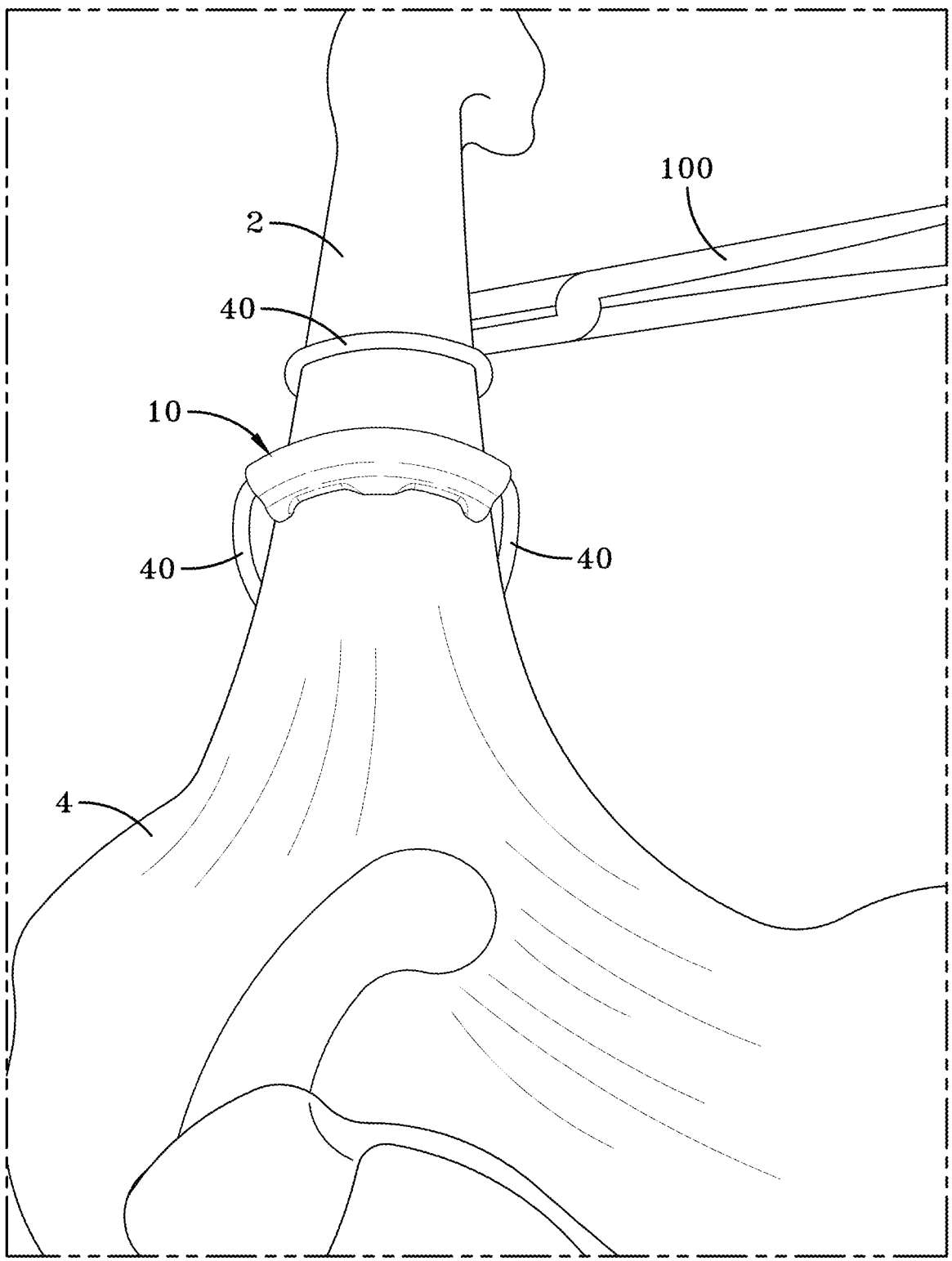
FIG. 16 shows a second depiction of the device being placed on a femur bone next to the head of the femur and a cable without a spacer for comparison.

The present invention increases the contact area to bone such that the cable 40 is restricted from penetrating the bone 2 as the cable 40 is tensioned. This prevents additional fracturing of the bone 2. It also improves the mechanical strength of the fracture repair construct. FIG. 16 illustrates a comparison of an exemplary cable 40 alone and the cable 40 when coupled to the improved bone repair or stabilization device 10 with a spacer body 11. Improved distribution of contact forces between the tensioned cable 40 and the fractured bone 2 is shown.

Stainless Steel, titanium, or any other non-corrosive material, whether permanent or resorbable can be used to make the spacer body 11.

The present invention improves the repair of periprosthetic hip fractures. Currently a cable tensioned around a PPHF penetrates the proximal femur resulting in secondary femur fractures and loss of fixation of the periprosthetic fracture repair construct. The present invention limits and prevents cortical penetration of a tensioned cable. Thereby the fracture is stabilized, which permits fracture union.

The strength of any bone is directly proportional to how much of a load it bears from day-to-day. This process is very similar to muscle size and strength. Working out, exercising and lifting weights will result in increased muscle mass and strength. The same principle applies to bone. Normally, human bone is very tough and feels hard to the touch. Osteoporosis, is one circumstance whereby bone loses its strength. Another situation where bone becomes weaker is when it contains a metal implant. The femur or thigh bone on the occasion of a hip replacement has a metal stem placed in the upper portion of it. When this hip stem sits in the upper femur for a period of time, the surrounding bone weakens. This weakening is due to stress shielding. The process of stress shielding simply means that the metal stem bears all of the load with standing and it shields the adjacent bone from the stresses or work of standing. This may at first sound like a favorable process, except the bone that is shielded from stress will weaken slowly over time. The end result is twofold. First, the hip stem may loosen. Secondly, a periprosthetic femur fracture (PPFF) will occur more easily in the upper part of the thigh bone. Repair of a PPFF is challenged by the presence of the hip stem. The hip stem limits passage of screws across the width of the broken bone because the hip stem is in femoral canal. The best option at this point to fix a PPFF is to use cables. Except, the bone is weak and any cable tightened around the bone will simply cut into the bone and lose the ability to hold a fracture in place until it heals. A simplistic analogy would be to imagine a warm knife cutting through butter. The cables that are currently available for PPFF repairs are commonly only 1.7 mm in width or diameter, typically between 1.6 mm and 2.0 mm in width or diameter. This narrow width or diameter is part of the problem and why cables around a PPFF do not provide any fixation. The solution this invention offers is to pass a spacer 11 with feet 20 that are wider than the cable 40 over the cable 40, preferably by passing the cable 40 through an aperture in the spacer 11. The feet 20 are twice the width or diameter of a cable 40. The spacer 11 has two feet fore or leading and two feet after or trailing. Every foot 20 has a diameter or width twice the width of a cable 40. Accordingly, for a cable diameter of 1.5 mm to 2.0 mm, each foot will have a width of 3.0 mm to 4.0 mm or greater. Therefore, the two fore or leading feet offer four times the surface area of a cable 40. Likewise, the two after or trailing feet 20 offer four times the surface area of a cable 40. This increased surface area of the feet 20 on the cable spacer 11 improves the fixation of a cable 40 tensioned around a stress shielded bone 2 because the cable 40 cannot cut into the weakened bone 2. A simplistic analogy would be to imagine trying to pass a spoon through butter.

These features are explained in reference to the detailed drawings. In some embodiments, the spacer 11 is a single piece structure with an arcuate or curved shape to fit about an exterior surface of the bone 2. This single piece structure typically extends about 90 degrees to 180 degrees, but can extend from 15 degrees to 180 degrees, preferably 30 degrees or 45 degrees to 180 degrees. In other embodiments, the spacer 11 has a short circumferential arc of say 30 degrees to 60 degrees or 15 degrees to 90 degrees and can be stacked in a plurality of such spacers 11 around a cable 40 to create a variety of circumferential or arcuate lengths extending around the bone 2 to completely encircle the bone 2 up to 360 degrees if so desired. Normally this encirclement can be less than that to achieve the desired protection of the bone 2.

Figure 1:
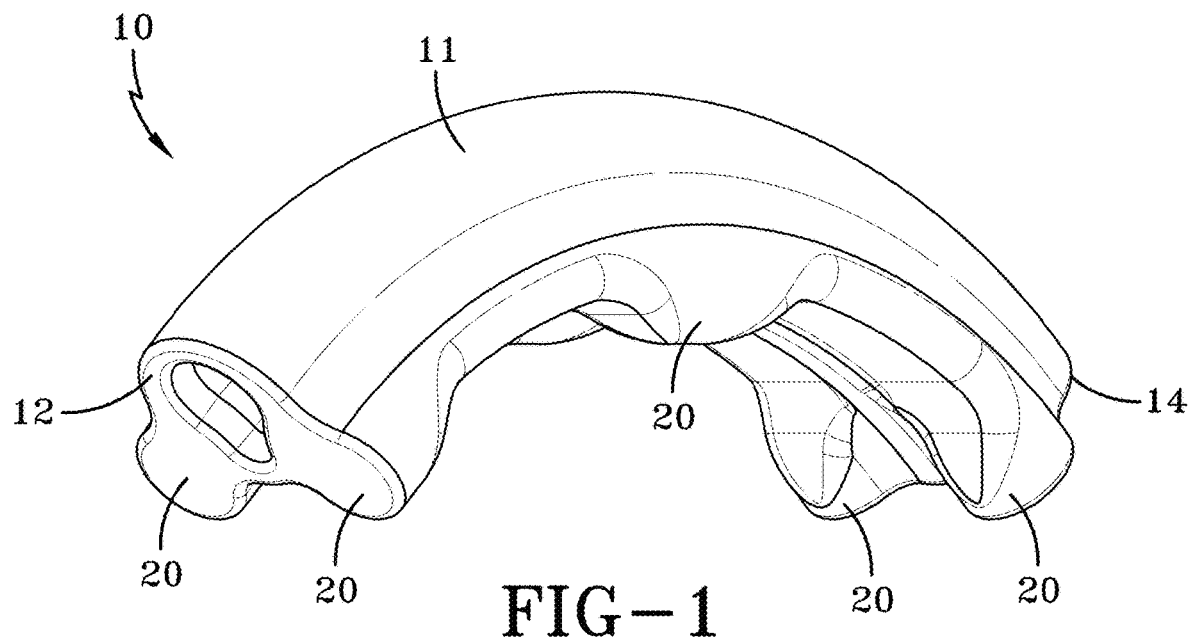
FIG. 1 is a perspective view of an exemplary embodiment of the improved fracture cabling device according to the present invention.

With reference to FIG. 1, a perspective view of the device 10 of the present invention is illustrated. The device 10 has the spacer body 11, the spacer body has a leading end 12 and a trailing end 14. Positioned on the inner circumferential arc of the spacer body 11 are a plurality of feet 20. The feet 20 at a leading end 12 and the feet 20 at a trailing end 14 are approximately half the length of the feet 20 as illustrated in the intermediate position at the midpoint of the arc of the spacer 11.

Figure 2:
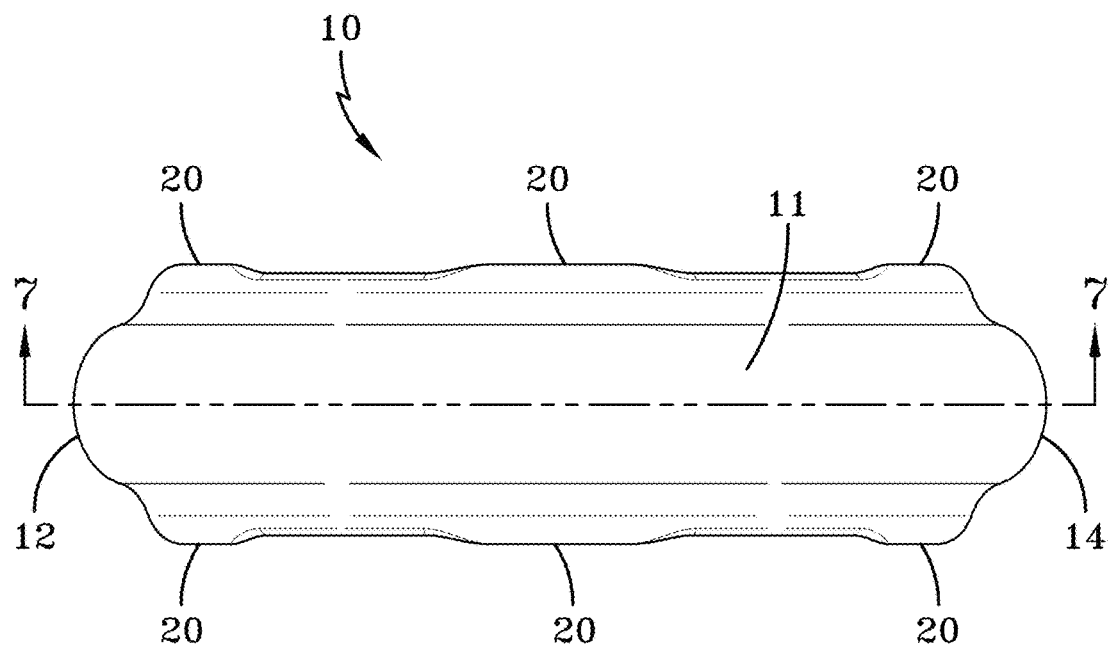
FIG. 2 is a top plan view of the device shown in FIG. 1.

With reference to FIG. 2, a plan view of the spacer body 11 of the device 10 is illustrated showing the leading end 12 and the trailing end 14 with the plurality of feet 20. The feet 20 as shown are on both sides of the device 10 at lateral extremes.

Figure 3:
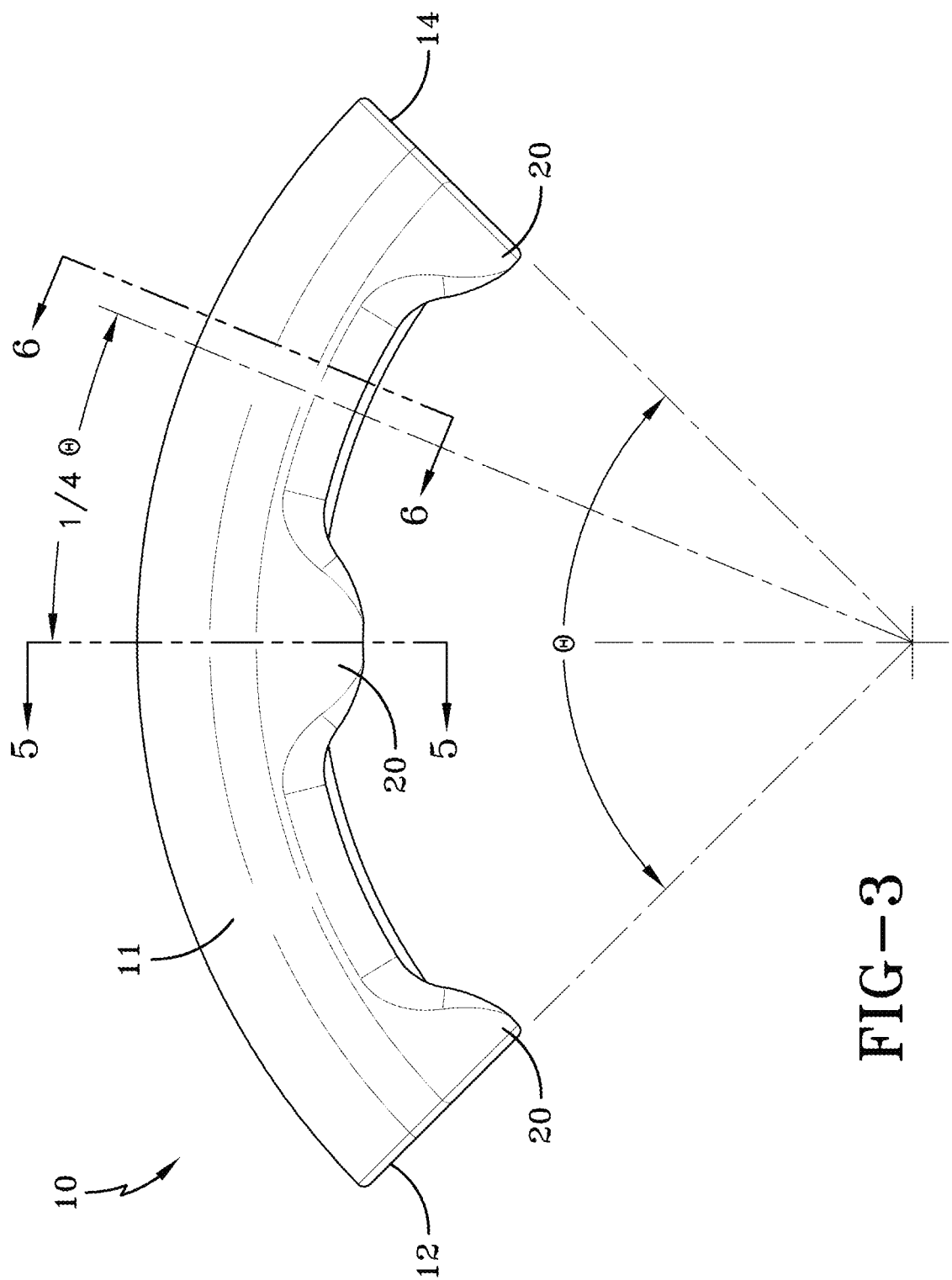
FIG. 3 is a side view of the device shown in FIG. 1.

With reference to FIG. 3. A view of the spacer body 11 of the device 10 is illustrated. As shown, the device 10 extends about an arc θ, as illustrated θ is a circumferential arc. It can be made as a single radius of curvature or a plurality of curvatures. The important aspect is that the arc θ extends angularly about 90 degrees as illustrated in this embodiment. As shown, a ¼ angle θ is shown between the intermediate foot 20 and the spacer body 11. The feet 20 at the trailing and leading ends 12, 14 are approximately half the extension of the intermediate feet. The intermediate feet are a full rounded curvature whereas the leading and trailing end feet 20 are cut at those ends and represent about half the circumferential or longitudinal length of the intermediate feet 20. In other words, the intermediate feet 20 will be twice the amount of contact area with regard to the bone 2 when assembled whereas the leading and trailing end feet are approximately half the length.

Figure 4:
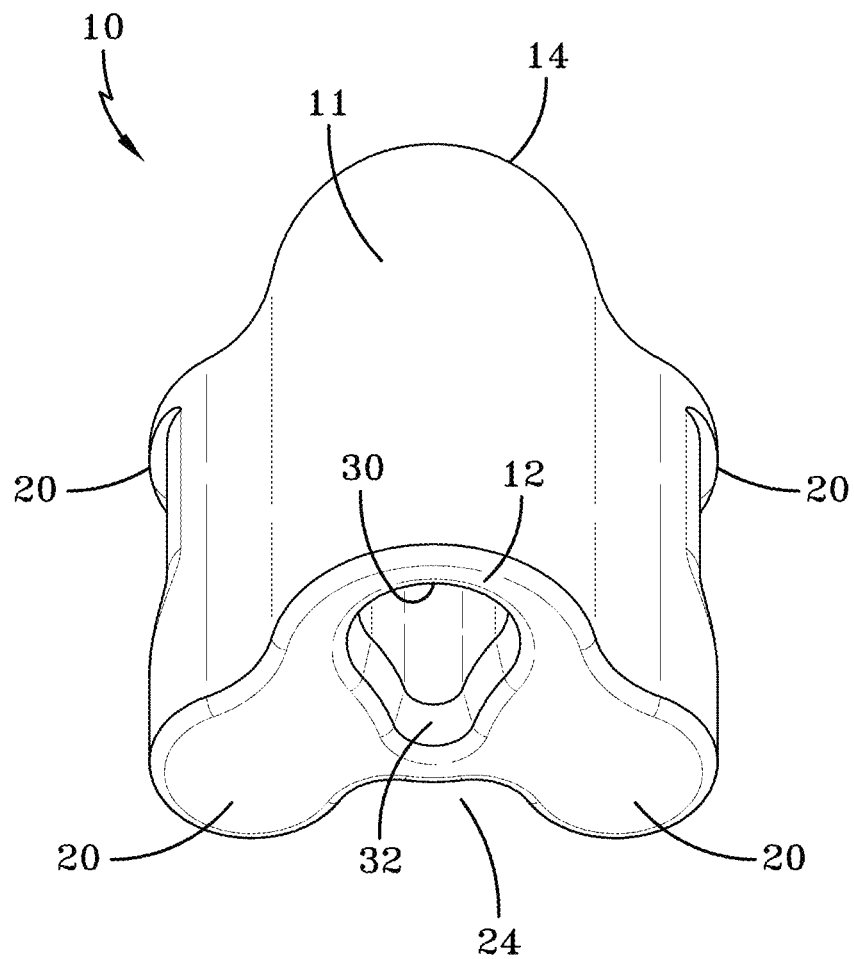
FIG. 4 is an end view of the device shown in FIG. 3.

Importantly, with reference to FIG. 4, when looking at an end view of the spacer 11 of the device 10 shows the leading end 12 feet 20 spaced by a gap 24. The gap 24 spaces the feet 20 in pairs about the longitudinal or arcuate length of the spacer body 11. As illustrated, these feet 20 have a radius of curvature 20R, as discussed earlier this radius of curvature 20R is approximately, in this example, 3.4 mm in diameter which is approximately twice that of the 1.7 mm diameter of the cable 40 to which it will be attached. As further illustrated in FIG. 4, an aperture 30 is shown that has a rounded or circular shape for receiving a cable 40. At the 6 o'clock position or lower portion of this aperture 30 is a slotted opening 32 that communicates with aperture 30. This slotted opening 32 is narrow and provides a way of localizing the cable when it is inserted through the aperture 30. This central narrow slotted opening 32 secures the cable 40 in such a fashion that it cannot translate or shift left or right, but is always centered even upon tensioning of the device 10 which will be discussed later.

Figure 5:
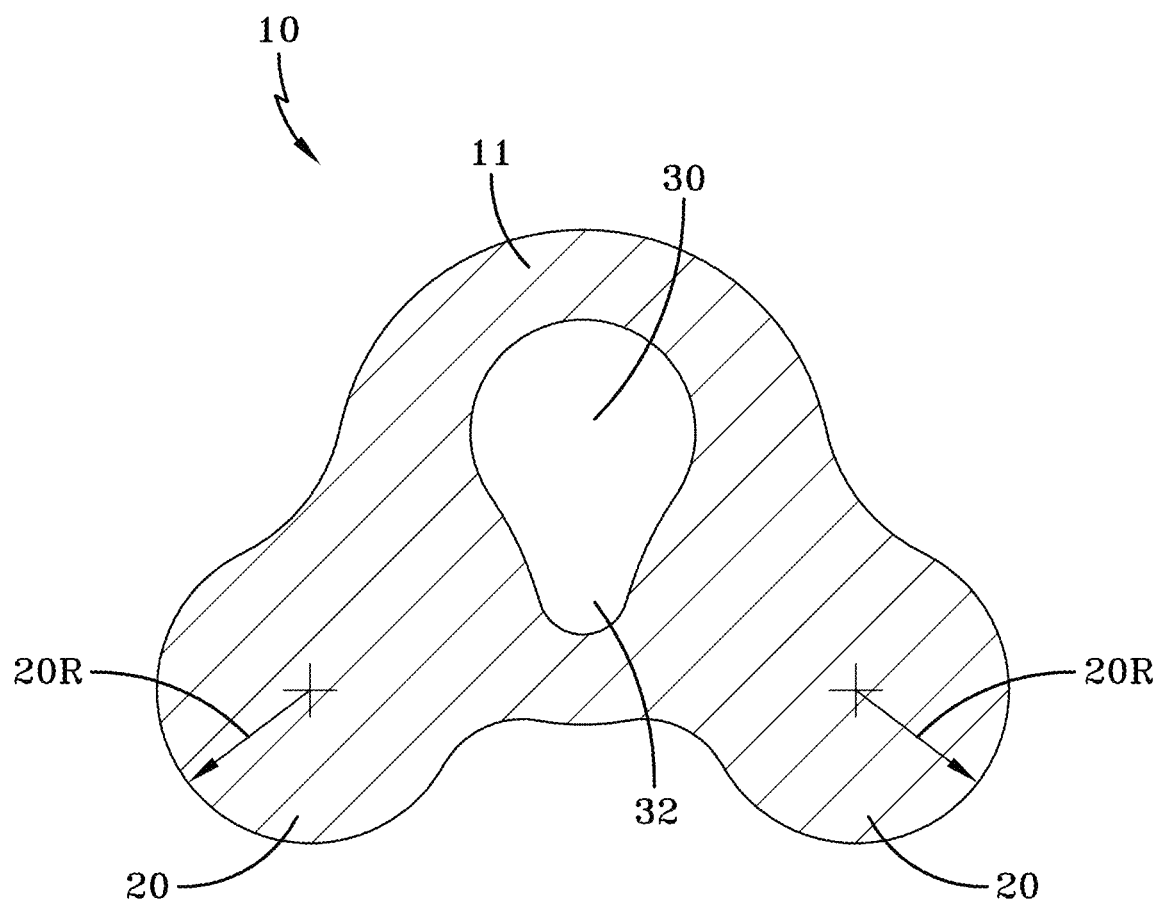
FIG. 5 is a cross-sectional view of the device shown in FIG. 3 taken along section 5-5.

With reference to FIG. 5, a cross sectional view better illustrates the aperture 30 and slot 32. As can be seen, a cable 40 when positioned through the opening 30 will tend to center itself on the slot 32 and upon tensioning will tightly secure the device 10. As further shown the feet 20 has a radius of curvature 20R as discussed. As shown, this radius of curvature 20R is approximately twice that of the size of the typical cable 40. This is important as when the device 10 or spacer body 11 is pressed tightly against the bone 2, the objective is to have a larger contact area so it reduces bone penetration while providing contact with the bone 2 in this spaced orientation. As can be appreciated, the gap 24 between the feet 20 as illustrated provide a space. This effectively means that when the spacer body 11 is positioned over a fracture, the feet 20 can straddle the fracture if so desired, in such a fashion that they will provide contact on both sides of the fracture without necessarily having to lie directly into the broken bone pieces. This further facilitates the use of this device in such a fashion that it can secure and better provide a contact region that is less damaging to the bone 2, particularly a fractured bone.

Figure 6:
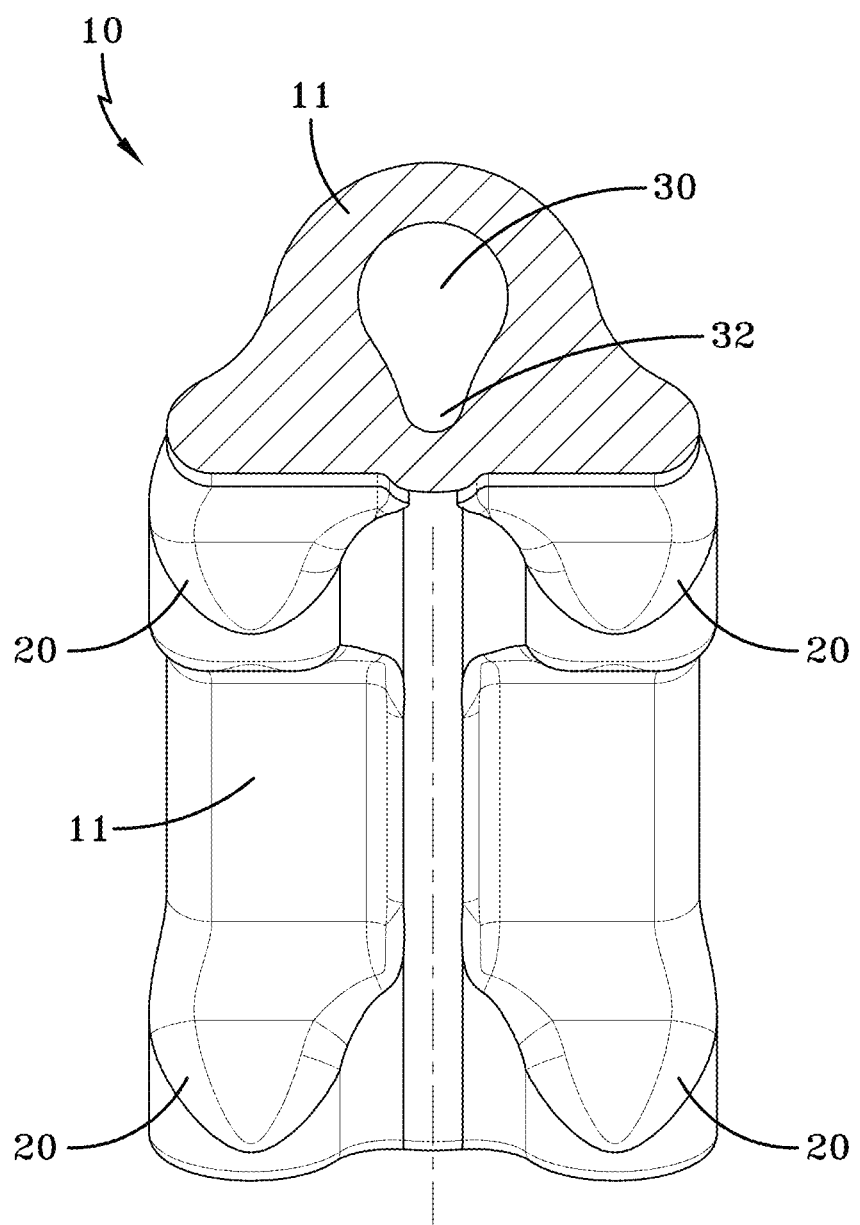
FIG. 6 is a cross-sectional view of the device shown in FIG. 3 taken along section 6-6.

With reference to FIG. 6, an end view of the device 10 is shown with a cross section showing the aperture 30 and the slotted opening 32 communicating with the aperture 30. The spacer body 11 is further illustrated from an underside view. In the underside view the feet 20 are shown in this section 6-6.

Figure 7:
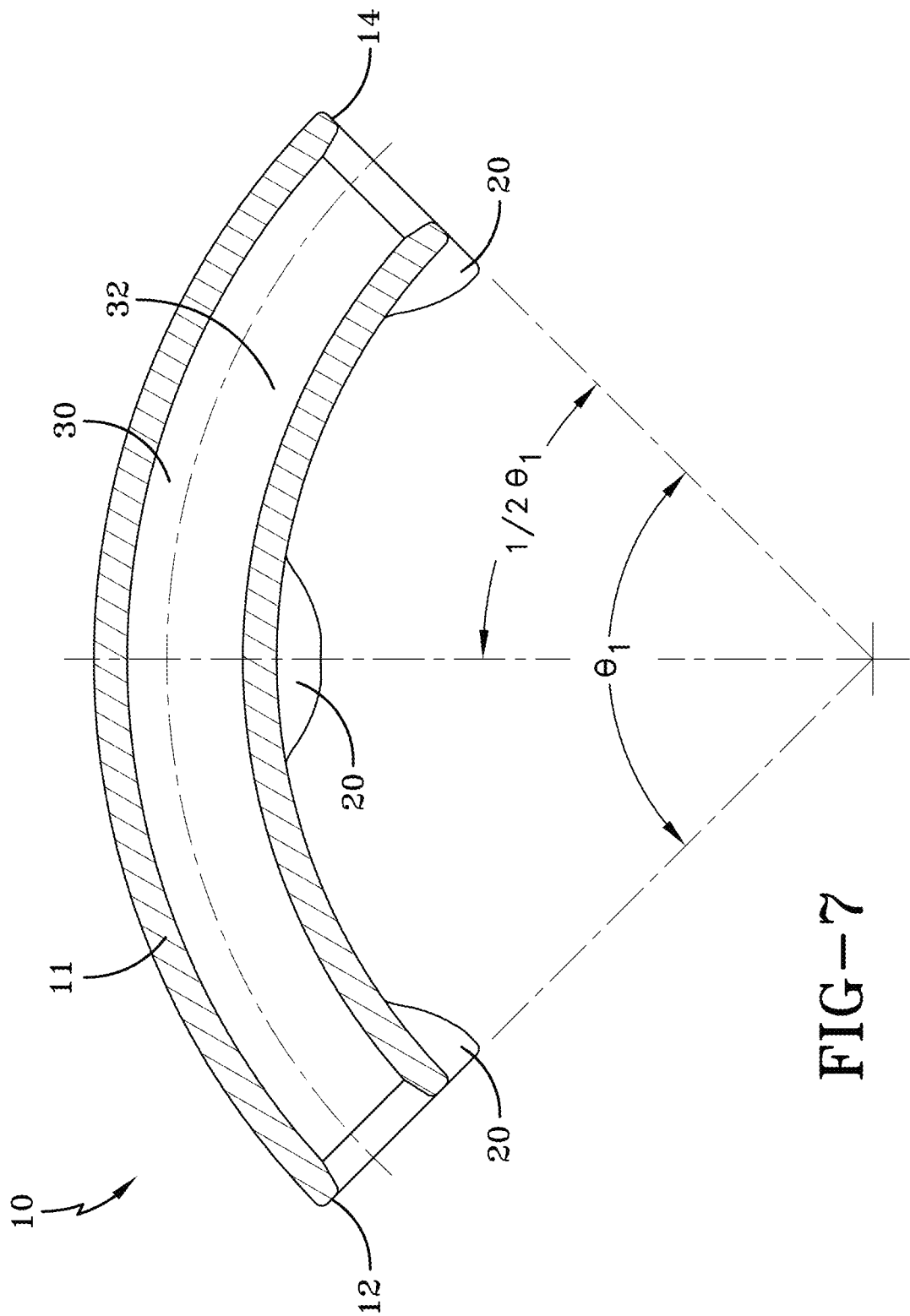
FIG. 7 is a cross-sectional view of the device shown in FIG. 2 taken along section 7-7.

With reference to FIG. 7, a cross sectional view of the device 10 as taken along the circumferential length of the spacer body 11. This spacer body 11 greatly shows how the aperture 30 extends through the leading end 12 through to the trailing end 14 as does the slotted opening 32 at the bottom of the aperture which centrally localizes the cable 40 such that it will securely fit always in the bottom of the aperture 30. As illustrated, the feet 20 at the leading and trailing ends 12, 14 are approximately half the circumferential or longitudinal length of the intermediate foot 20.

Figure 8:
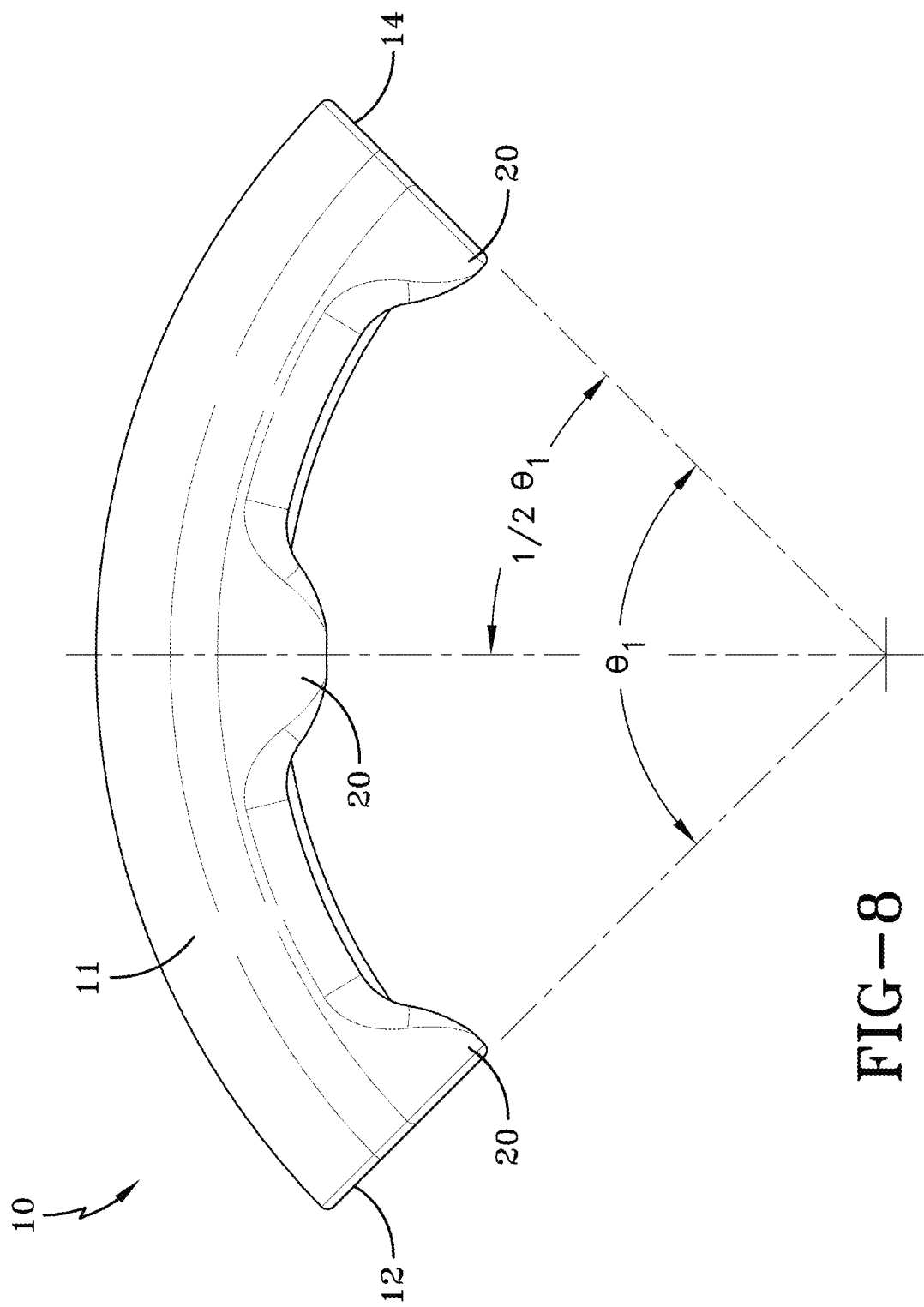
FIG. 8 is a side view of the exemplary embodiment of the spacer for improved bone fracture system.

With reference to FIG. 8, a first embodiment of the invention device 10 is shown. In this embodiment the angle $\theta_1$ is approximately 90 degrees. The distance from the end to the center of the feet 20 at the intermediate location is approximately 45 degrees on either side from the leading 12 or trailing end 14.

Figure 9:
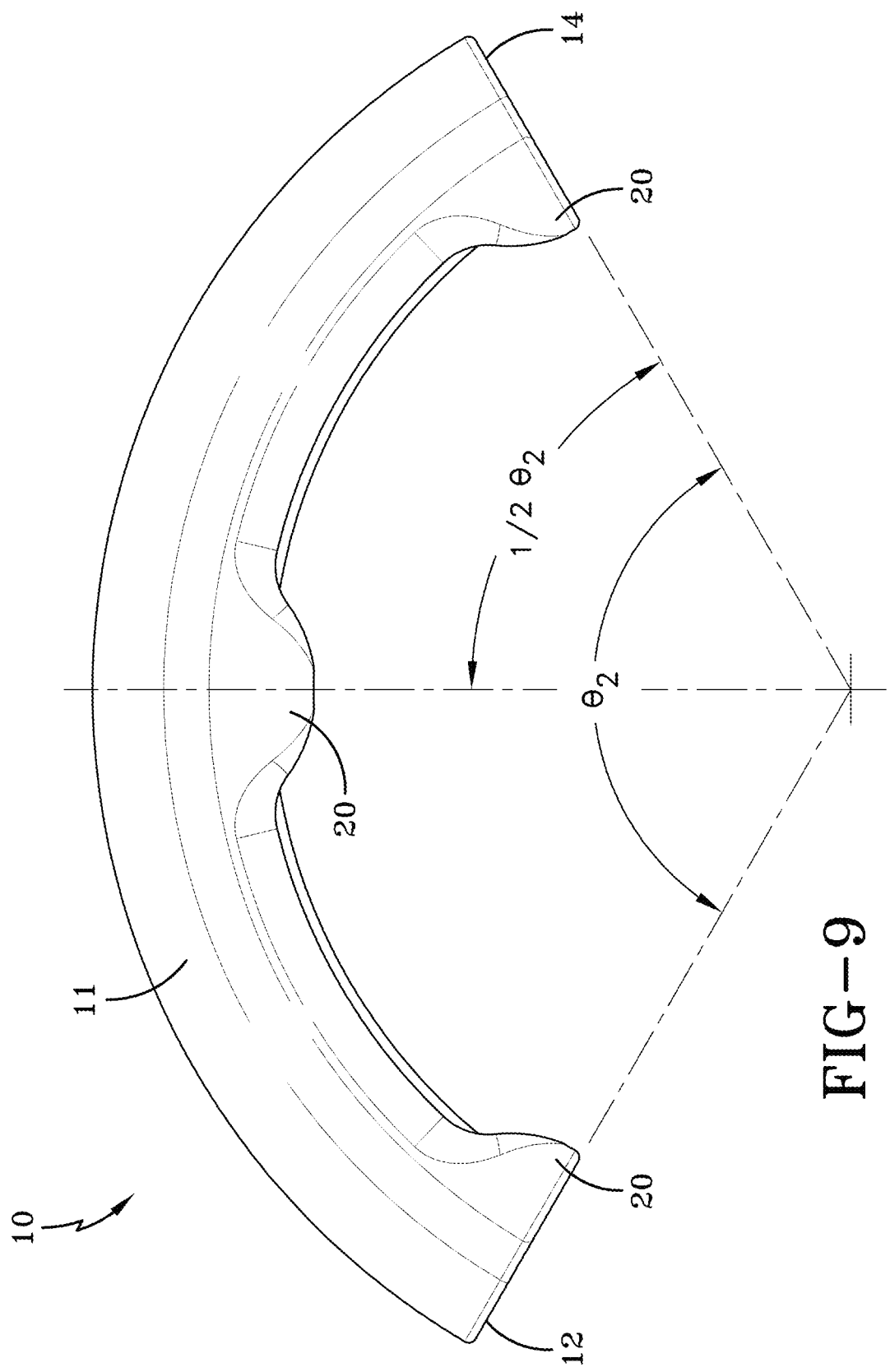
FIG. 9 is a side view of a second embodiment of the spacer for improved bone fracture system.

In a second embodiment shown in FIG. 9, the device 10 is shown wherein the spacer body 11 extends 120 degrees. In this embodiment $\theta_2$ is 120 degrees. As shown half of $\theta_2$ is approximately 60 degrees. This is the dimension that extends from the leading or trailing feet 20 to a mid-portion of the intermediate feet 20.

Figure 10:
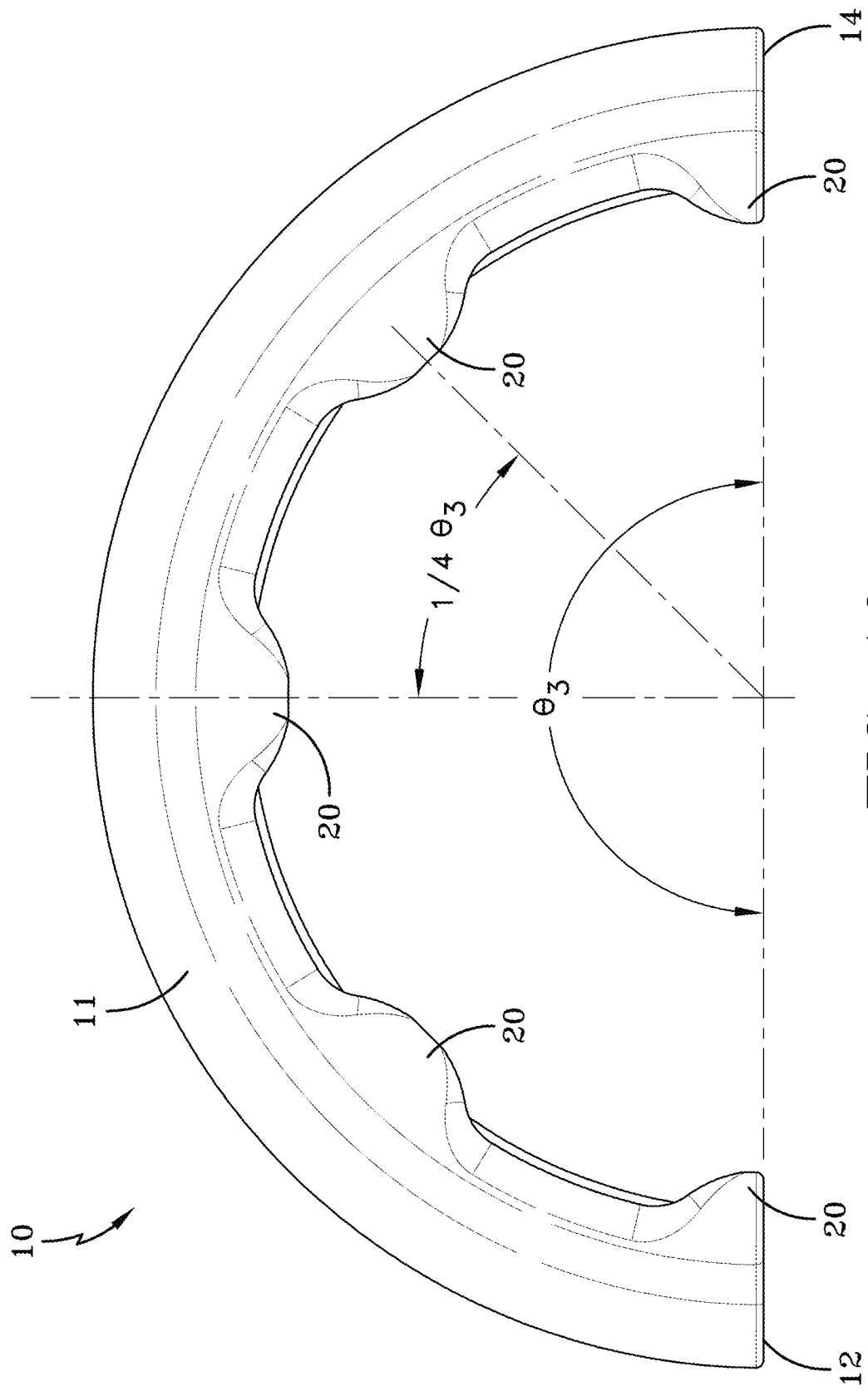
FIG. 10 is a side view of a third embodiment of the spacer for improved bone fracture system.

With reference to FIG. 10, a third embodiment device 10 is shown where the spacer body 11 extends a full 180 degrees longitudinally. In this embodiment, as illustrated, the leading end 12 and trailing end 14 each have the feet 20 adjacent the end half the size of the three intermediate feet 20 in this embodiment. The angle $\theta_3$ is shown at 180 degrees. The distance between adjacent feet along the circumferential length is approximately ¼ $\theta_3$ or 45 degrees in this embodiment.

Figure 11:
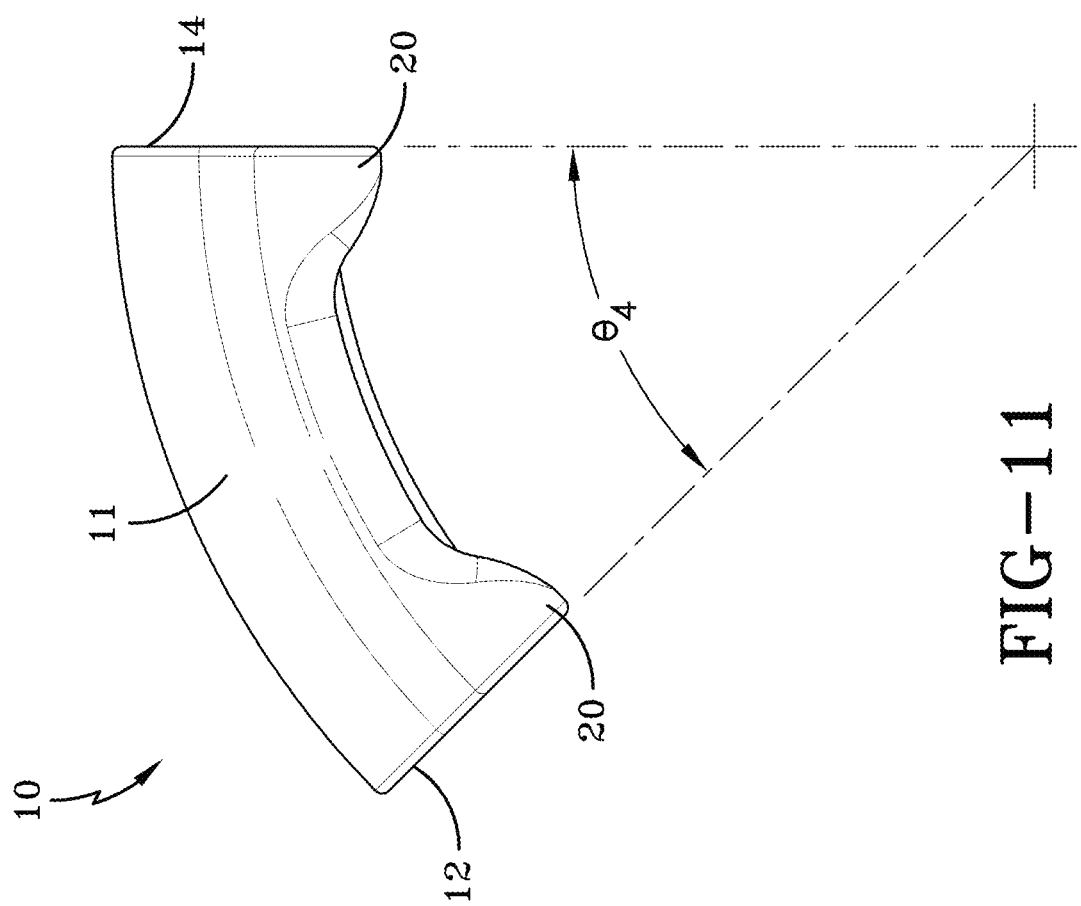
FIG. 11 is a side view of a fourth embodiment of the spacer for improved bone fracture system.

With reference to FIG. 11, a fourth embodiment device 10 is shown. This embodiment is smaller in circumferential length than the other embodiments illustrated. In this embodiment, the leading end 12 and trailing end 14 have the feet 20, but there are no intermediate feet 20. In this embodiment the angle $\theta_4$ is approximately 45 degrees as illustrated. This 45 degree angle extends from the leading end 12 to the trailing end 14 along the circumferential length of the spacer body 11.

Figure 12:
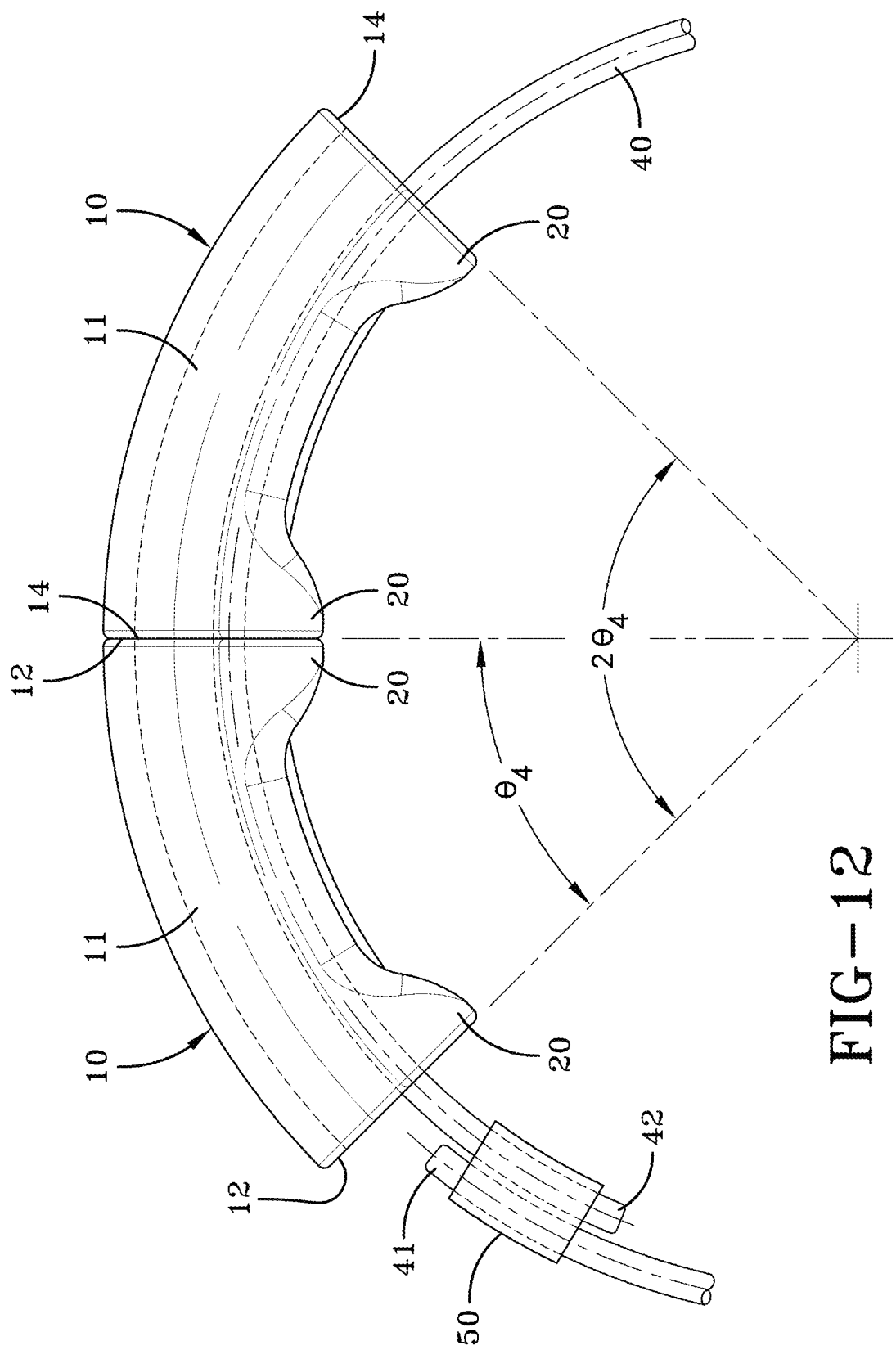
FIG. 12 is a side view of the fourth embodiment with two spacers and a cable and cable crimp shown.

As illustrated in FIG. 12, when the spacer 11 of the fourth embodiment is stacked about a cable 40, two spacers 11 can be used to create a 90 degree device. When stacked the leading end 12 and the trailing end 14 of an adjacent spacer 11 will abut and when tensioned because of the slotted opening 32 in the aperture 30 that causes the cable 40 to tension and always be centered, the abutting leading 12 and trailing end 14 feet in combination will create full size or rounded bone contacting feet similar to the intermediate feet 20 of other embodiments. While the bone 2 is not always at the proper radius of curvature, the advantage of using stacked or a plurality of spacers 11 to tension the cable 40 provides feet 20 for maintaining contact tightly against the bone 2 such that there is not gap or space between the spacers 11.

Figure 13:
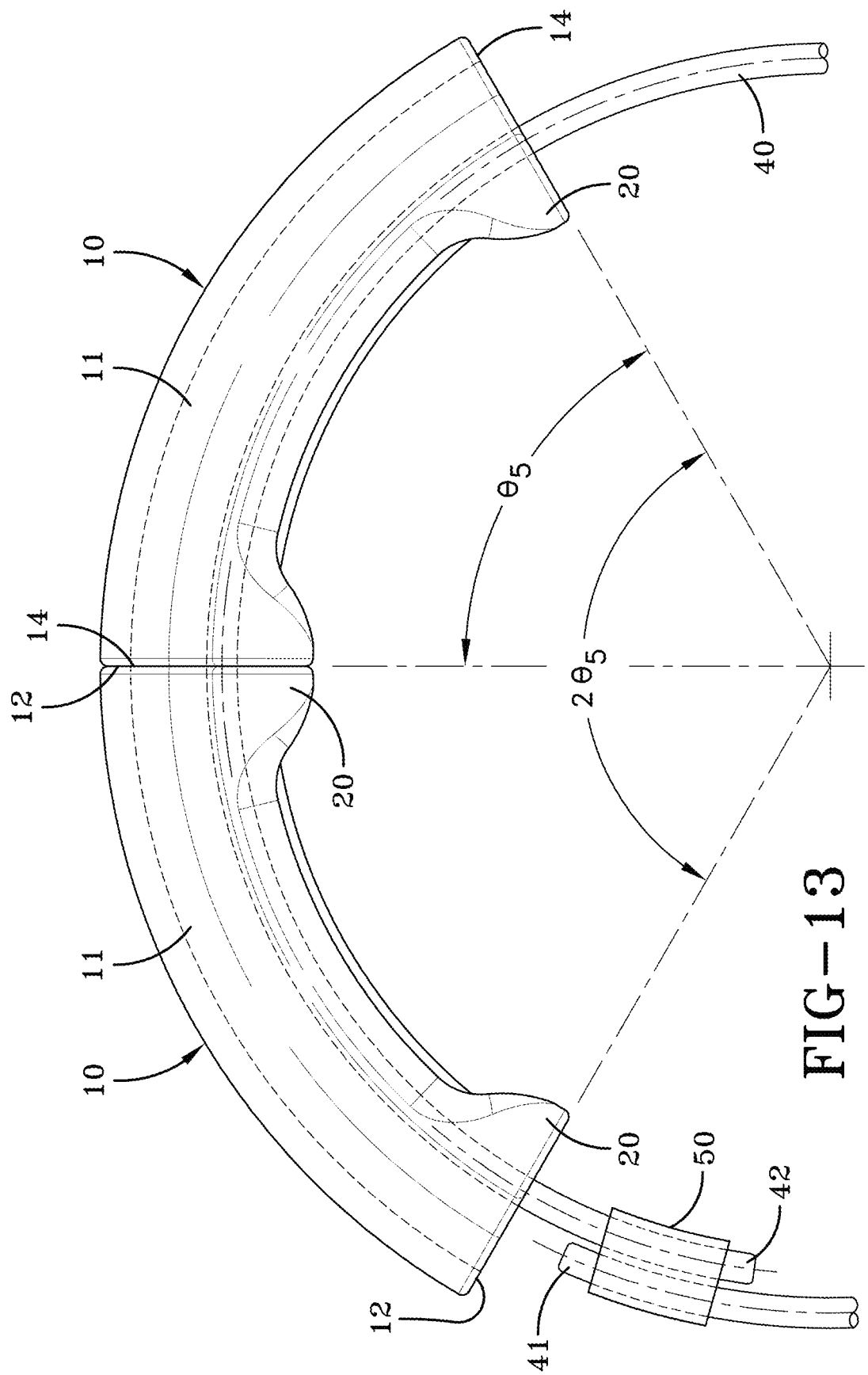
FIG. 13 is a side view of the fourth embodiment with two spacers and a cable and cable crimp shown.

With reference to FIG. 13, an embodiment 5 is illustrated wherein the spacer body 11 extends approximately 60 degrees or angle $\theta_5$ by stacking two of these spacer bodies 11 together, an angle is achieved of 205 or 120 degrees.

When the cable 40 is passed through the opening 30, the cable 40 can be crimped together by a crimping device 50 that allows one end of the cable 42 to be positioned in the crimping device 50 and the other end 41 to be inserted through another opening in the cable crimping device 50. Therefore, when tensioned and crimped, the embodiments will be held in positioned tightly against the bone 2.

Figure 14:
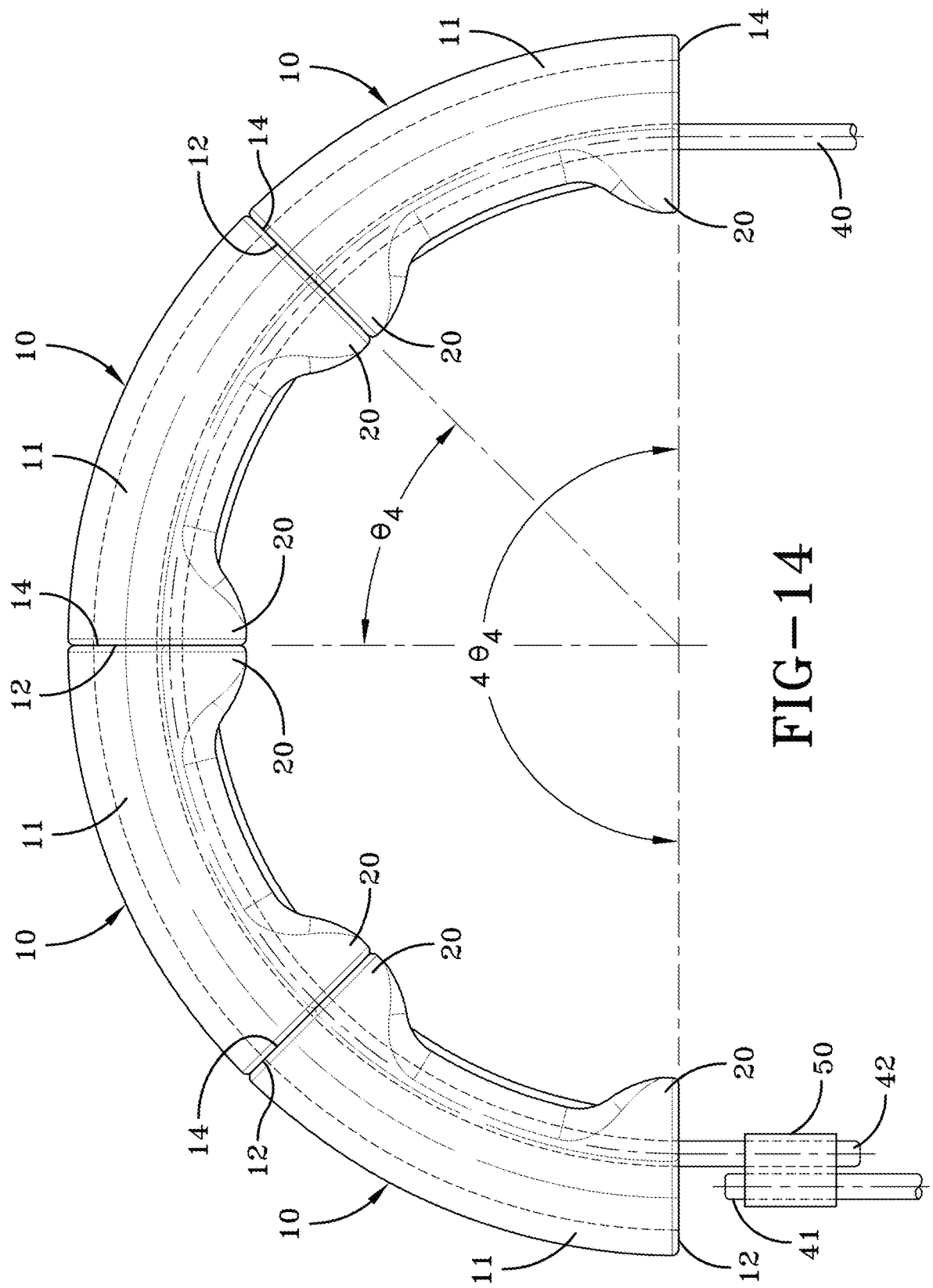
FIG. 14 is a side view of the fourth embodiment with four spacers and a cable and cable crimp shown.

In FIG. 14 another embodiment is illustrated wherein the four spacer bodies 11 are stacked along a cable 40. These four spacer bodies 11 have an approximate angle $\theta_4$ of 45 degrees. Stacking four of the $\theta_4$ spacers circumferentially about the cable 40 allows for a 180 degree device 10 to be created. Again, as illustrated, the crimping device 50 that holds the cable ends 41, 42. What happens the end 42 in the embodiment shown can have a bulbous end. This is not required, however, it provides an additional feature to make it easier for the surgeon to tension the cable 40.

Figure 15:
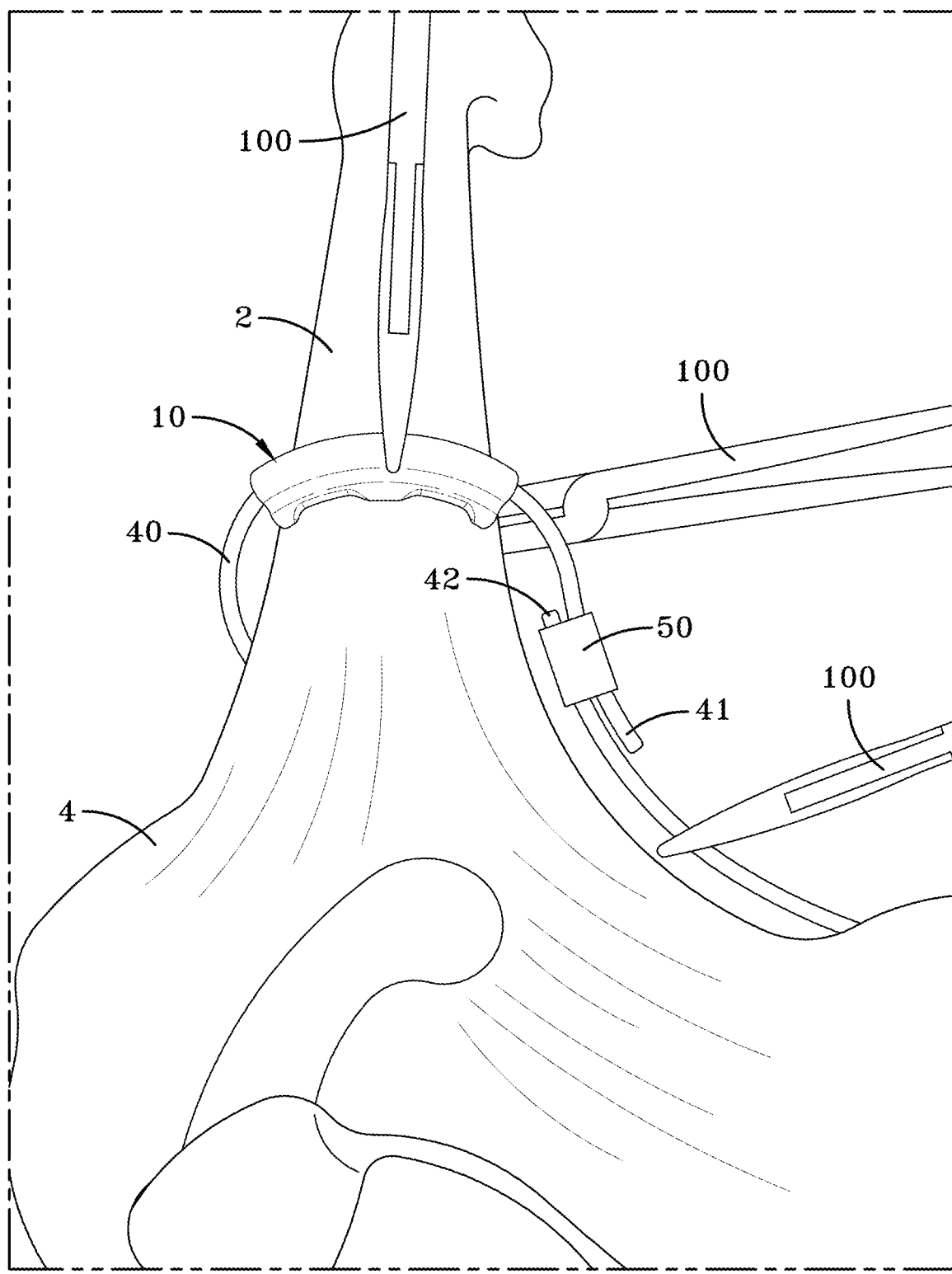
FIG. 15 shows a depiction of the device being placed on a bone.

With reference to FIGS. 15 and 16, the device 10 of the present invention is shown. In FIG. 15, the device 10 is shown with the 45 degree radius spacer 11 shown in FIG. 1. In this device 10 the cable 40 is shown being passed through the spacer body 11 and the tools 100 are shown pulling the cable 40 in such a fashion that they fit about the bone 2. As shown, the bone 2 has an enlarged femur head 4 and the encircling device 10 having a spacer 11 are shown slightly below this enlarged head 4 so they can stabilize the bone 2. FIG. 16 further illustrates a comparison of the spacer device 10 when tensioned about the bone 2 affixed to a bone 2 close to the femur head 4. For comparison purposes in FIG. 16, a cable wire 40 without the spacer device body 11 is shown to show how narrow the cable wire 40 is and how prone it is to penetrate into a weakened bone. Therefore, the use of the present invention 10 provides stabilizing feet 20 that are spaced out not only along a circumferential arc but also spaced laterally such that it provides a stability factor such that the device 10 will not tip and provides a contact area of each foot 20 that is larger approximately double that of a typical wire width. And by using pairs of feet 20 along this circumferential arc, the device 10 is stabilized and provides much less bone penetrating potential compared to just a single cable wire.

Alternatively, in the prior art, flat devices are commonly employed. However, these flat devices are limited in that they provide a flat surface around which the bone 2 is to be accommodated whereas the feet provide an arcuate shape that better contacts the bone 2 locally and provides a superior contact point that is stabilized due to the fact that the aperture 30 for receiving the cable 40 has a slot 32 that centralizes the cable 40 in such a fashion that it cannot shift. This allows the radially inner portion of the spacer 11 to be stabilized by effective use of pairs of feet 20 on each lateral side of the device 10.

Figure 17:
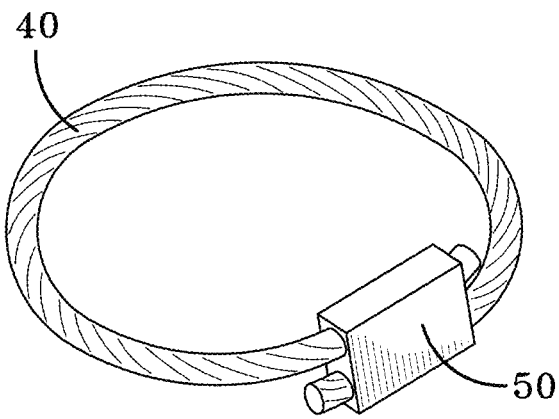
FIG. 17 shows an exemplary wire and crimp.

With reference to FIG. 17, a typical cable 40 is shown with a crimping device 50. This is provided simply to illustrate how the crimping device 50 works wherein pairs of openings 52 are provided, each opening 52 to receive an end of the cable 40. This simplifies the procedure for the surgeon.

Figure 18:
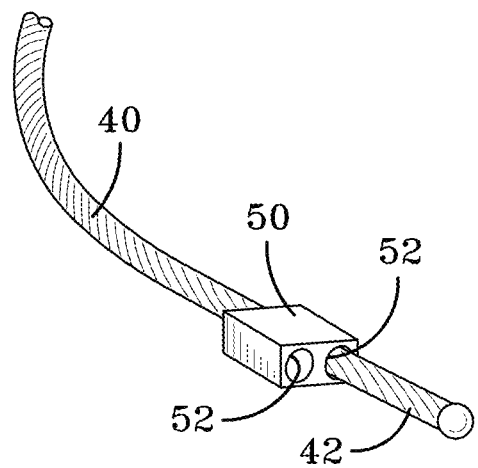
FIG. 18 shows an alternative exemplary wire with a ball end and a crimp.

As further illustrated in FIG. 18, one of the ends 42 of a cable 40 is illustrated with a bulbous end. This further facilitates the tensioning procedure in that the crimping device 50 can be slid to the bulbous end 42 so that when the cerclage cable wire 40 is tightened against the bone 2 with the device 10 in place, it can be held easily in position. The surgeon only has to deal with the one end of the cable 40 to feed it through the crimping device 50 and tension it into the aperture 52. Upon crimping, the cable 40 will no longer move.

Figure 19:
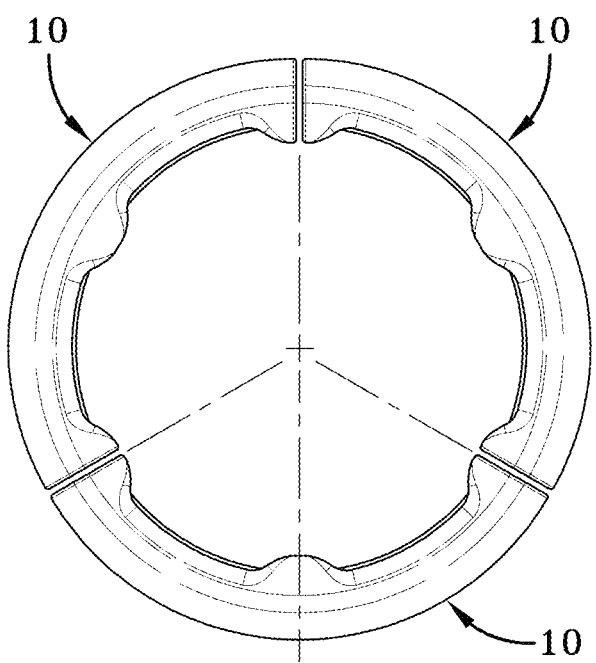
FIG. 19 shows the device of the present invention in a complete encircling configuration approaching 360 degrees.

With reference to FIG. 19, it is possible to use the device 10 in such a fashion that it completely encircles the bone 2 approximately 360 degrees. While this is not necessarily required in all circumstances, it provides a wonderful view of how the use of a plurality of spacer bodies 11 can be positioned in such a fashion that it can extend from as low as 90 degrees to as high as 360 degrees.

Figure 20:
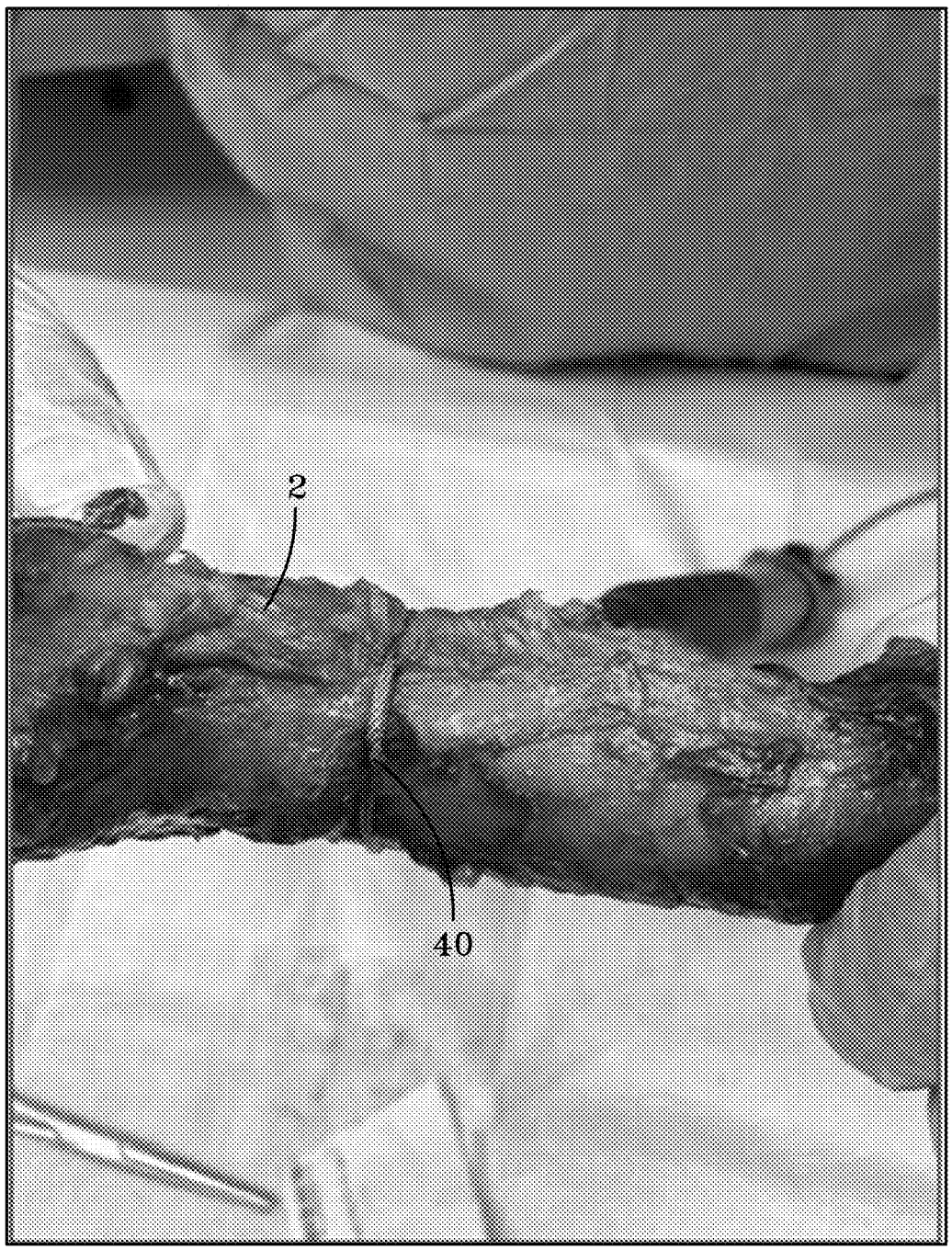
FIG. 20 is a photograph of a cable tensioned around a non-osteoporotic femur.
Figure 21:
FIG. 21 is a photograph of a cable tensioned a cadaver femur with a total hip stem.
Figure 22:
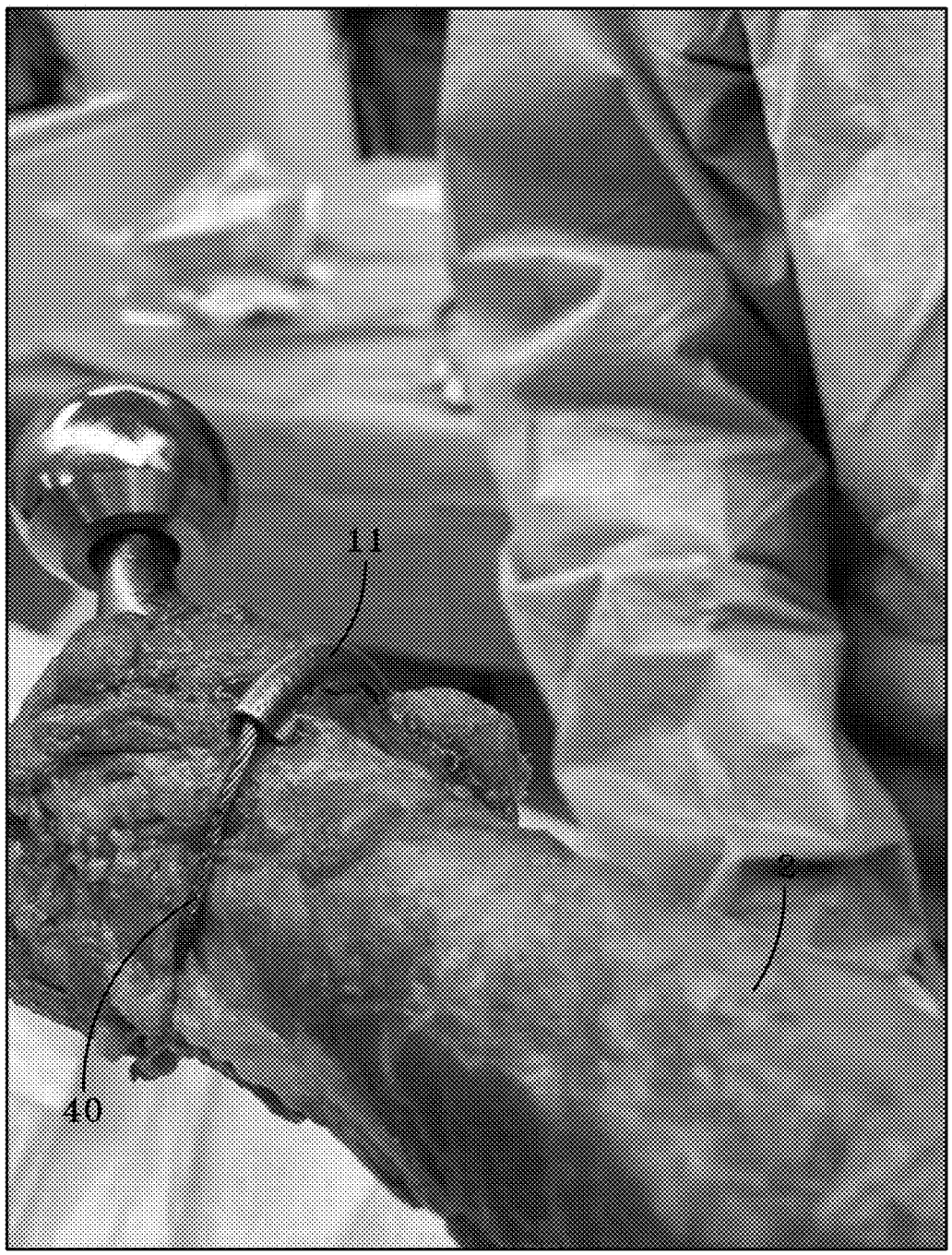
FIG. 22 is a photograph of a cable that has been passed through the present invention spacer, wrapped around a cadaver femur with a total hip stem, and tensioned to the cable manufacturer's recommended tension level.
Figure 23:
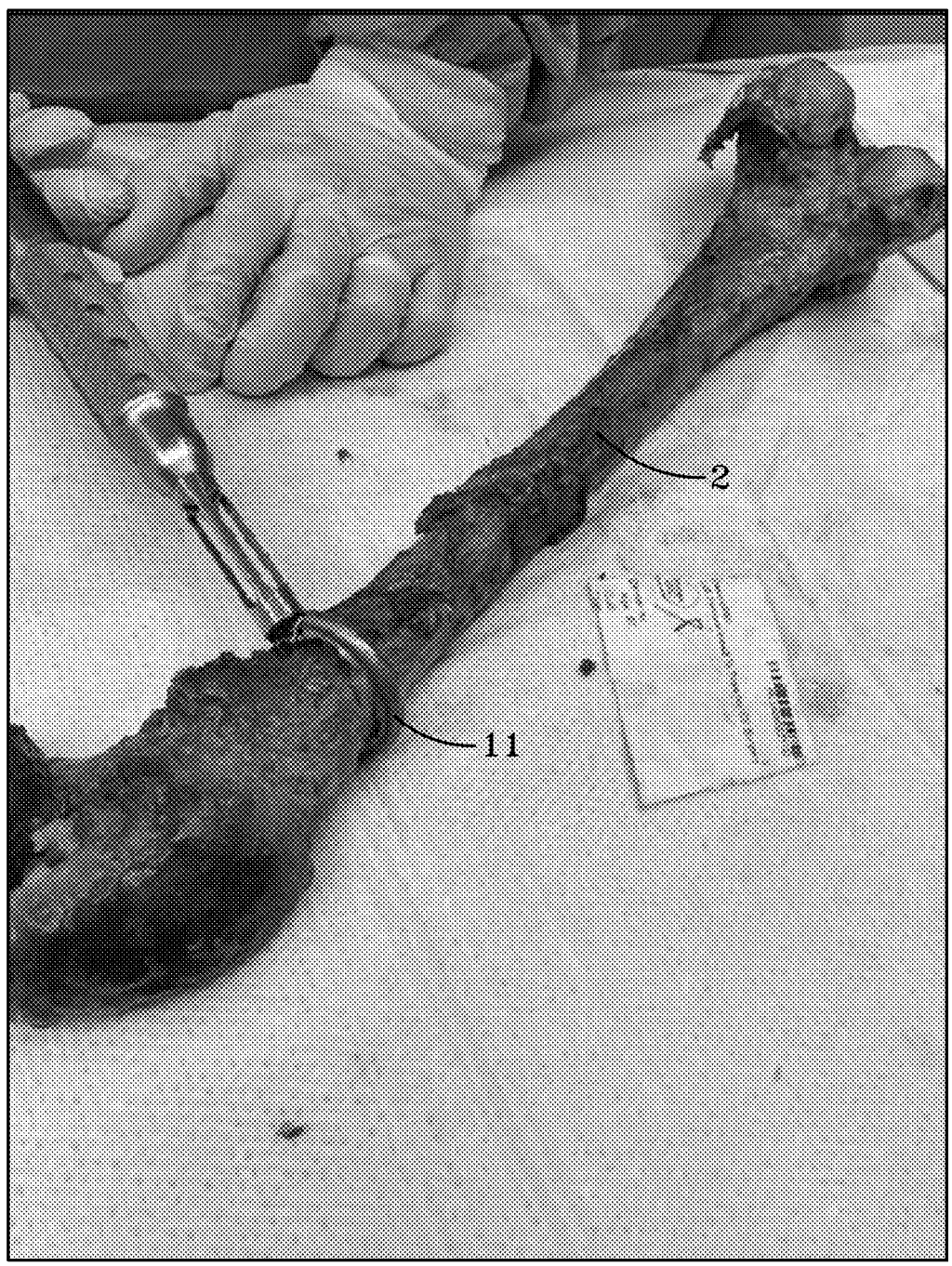
FIG. 23 is a photograph of a cable that has been passed through the present invention spacer, wrapped around a cadaver femur, and tensioned to the cable manufacturer's recommended tension level.

The photographs of FIGS. 20-23 show cables 40 alone and cables 40 with the spacer 11 of the present invention used on periprosthetic fractures. The photograph of FIG. 20 shows a cable 40 tensioned around a non-osteoporotic femur bone 2. Note the cable 40 has constricted the overlying soft tissues, but the cable 40 has not penetrated the cortex as is seen in FIG. 21. In FIG. 21, a cable 40 was tensioned just proximal to the lesser trochanter of a cadaver femur 2 with a total hip stem. The tip of the cable is pointing to where the cable 40 penetrated the femur 2. The photographs of FIG. 22 shows a cable 40 has been passed through the new spacer 11, wrapped around a cadaver femur 2 with a total hip stem, and tensioned to the cable manufacturer's recommended tension level. Compare this to FIG. 21 and note how the spacer 11 prevents cable 40 penetration. The photograph of FIG. 23 shows a cable 40 has been passed through the new spacer 11, wrapped around a cadaver femur 2, and tensioned to the cable manufacturer's recommended tension level. Compare this figure to FIG. 21 and note how the spacer 11 prevents cable 40 penetration.

Fractures of the femur after a total knee or a total hip replacement procedure are common. These fractures are called periprosthetic fractures (PPF). They are increasing in frequency due to the steady increase in adult joint reconstruction procedures performed annually. There are two significant challenges in repairing a PPF. First, the joint replacement implants interfere with application of fracture repair implants, such as plates and screws. As a result, metal cables are used. Normally, in non-osteoporotic bone cables provide adequate circumferential placement around a femur without cable penetration as shown in the photograph of FIG. 20. Secondly, cables applied on bone near joint replacement implants do not hold well. Poor fixation by cables near a joint replacement implant is because the bone is osteoporotic due to stress shielding as shown in the photograph of FIG. 21. Essentially, the bone adjacent to a hip or knee joint replacement is too weak and soft to provide adequate fixation with a metal cable to stabilize a PPF.

The inventor of the present invention has directly observed cables penetrating femurs applied in PPFF repairs. He studied this phenomenon further by obtaining 24 cadaver femurs that had a hip arthroplasty stem in place for a minimum of 6 months. In every cadaveric femur specimen, the cable penetrated the femoral bone when tensioned to the cable manufacturer's recommended tension level as shown in FIG. 21. In an attempt to limit cable penetration in stress shielded femurs, the inventor made the spacer 11 according to the present invention to pass over the cable 40 before cable tensioning as shown in FIGS. 22 and 23. The present invention device 10 improves upon his previous patented cable spacer as described in U.S. Pat. No. 9,387,024 B2 issued Jul. 12, 2016. This new device also protects the periosteal blood vessels via limited contact design. This implant improves upon the limited contact concept by widening the limited contact points of the spacer. The widened contact points distribute the tensioning forces of the cable as it is tightened. This prevents cable penetration into a stress shielded femur.

It is believed that the improved device 10 will distribute the loads against the bone 2 in such a fashion that bone repair of a fracture or stabilization of a weakened bone as in a hip replacement can be achieved without inducing any further fractures to the bone 2. This greatly enhances the procedure and makes it more likely for a favorable outcome for those who receive hip or knee replacements. These and other attributes of the present invention are as claimed in the claims as presented hereinafter.

The radius of curvature in conjunction with the fore and aft feet provide limited contact of a cable around a femoral bone. This is similar to the previously published spacer The improved fore and aft feet design prevents cable penetration or cortical fracture in stress shielded femurs. This is a new feature and different than the published spacer. Ironically, the published spacer is all about limited contact, whereas this new spacer adds contact area slightly to distribute tensioning forces to prevent cable penetration and cortical fracture in stress shielded femurs.

Periprosthetic femur fractures (PPFF) near hip or knee replacements are common. PPFF have osteoporotic bone from stress shielding which limits the use of cables for fixation of a PPFF. Stress shielding is a bone remodeling process. Femoral bone stress shielding occurs within 6 months of a joint reconstruction procedure. When a metal implant is placed in the femur for a joint reconstruction procedure, it shields the adjacent bone from weight bearing loads. This is stress shielding. In response to decreased loads to bone adjacent to a total joint implant, the bone becomes less dense or osteoporotic. This can lead to fractures. The fractures are difficult to treat because the bone is weaker and less able to hold metal fracture repair implants such as plates, screws, or cables. We have observed that metal cables 40 penetrate the femur bone, and fracture stress shielded PPFF as shown in FIG. 21. The present invention avoids this complication.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims. The surgical access window described herein encompasses the dimensions presented and any and all variations applicable to the methods and surgical technique described directly or indirectly intended with this device.

What is claimed is:

1. A fracture cabling system comprises:
   at least one spacer, wherein the at least one spacer has a longitudinal length and a pair of lateral sides extending along a body of the at least one spacer, wherein the body has an upper portion with an aperture configured to receive a wire or cable and a lower portion having at least three pairs of feet, wherein two pairs of the at least three pairs of feet are longitudinally spaced apart from each other and a third pair of the at least three pairs of feet is positioned between the two pairs of feet, wherein the feet of each pair of feet are spaced by a longitudinal gap, wherein the feet of the at least three pairs of feet are each located adjacent to a respective one of the lateral sides of the body and configured to contact a bone with a fracture, wherein the feet of the at least three pairs of feet each include a bone contacting surface having a rounded profile in at least one cross-sectional direction thereof, wherein the bone contacting surface of the feet of at least one of the pairs of feet each extend partially along a length of the body of the spacer, wherein a shape of the feet of the third pair of feet is a first shape different than a respective shape of the feet of each of the two pairs of feet, and wherein the pairs of the feet and the longitudinal gap are jointly configured for enabling the longitudinal gap to be positioned over at least a portion of the fracture with each foot of a respective one of the pairs of feet positioned on a portion of the bone spaced away from the fracture.

2. The fracture cabling system of claim 1 wherein the longitudinal length of the at least one spacer is curved or arcuate.

3. The fracture cabling system of claim 2 wherein:
the at least one spacer has a leading end and a training end; and
the leading end and the trailing end are spaced arcuately between 15 degrees to 180 degrees.

4. The fracture cabling system of claim 2 wherein:
the at least one spacer has a leading end and a training end; and
the leading end and the trailing end are spaced arcuately from 90 degrees to 180 degrees.

5. The fracture cabling system of claim 1 wherein the third pair of feet is located equidistant between the two pairs of feet.

6. The fracture cabling system of claim 1 further comprises:
a cable, wherein the cable is inserted through the aperture of the at least one spacer and when tightened, secures the at least one spacer in contact with the bone securely to set the fracture.

7. The fracture minimizing cabling system of claim 1 wherein all of the feet of the two pairs of feet have the same shape.

8. The fracture cabling system of claim 6 wherein the feet of the at least one spacer has a width wider than the cable passed through the at least one spacer to increase the contact area of the at least one spacer such that penetration of the at least one spacer and or cortical compromise by the at least one spacer is prevented thereby providing a stable fracture fixation construct.

9. A bone stabilizing cabling system comprises:
two spacers, wherein each spacer has a longitudinal length and a pair of lateral sides extending along a body of the spacer, wherein the body having an upper portion with an aperture configured to receive a wire or cable and a lower portion having two pairs of feet, wherein the feet of each pair of the two pairs of feet are spaced by a longitudinal gap, wherein the feet of the at least two pairs of feet are each located adjacent to a respective one of the lateral sides of the body and configured to contact a bone in near proximity to a femoral head of the bone, wherein a first one of the pairs of feet is positioned at a leading end of the body of a respective one of the two spacers, wherein a second one of the pairs of feet is positioned at a trailing end of the respective one of the two spacers, wherein the two spacers are arranged in an end-to-end manner whereby one of the ends of a first one of the two spacers and one of the ends a second one of the two spacers are abutting each other, wherein adjacent ones of the feet at the abutting ends of the two spacers jointly form a respective one of a full-size foot having a first shape, wherein the full-size foot includes a bone contacting surface having a rounded profile in at least one cross-sectional direction thereof, wherein the bone contacting surface of each of the full-size foot extends partially along a length of the body of a respective one of the spacers, and wherein the pairs of the feet and the longitudinal gap are jointly configured for enabling the longitudinal gap to be positioned over the bone with each foot of a respective one of the pairs of feet positioned on a portion of the bone spaced away from the femoral head to stabilize and reinforce the bone.

10. The bone stabilizing cabling system of claim 9 wherein the longitudinal length of each of the spacers is curved or arcuate.

11. The bone stabilizing cabling system of claim 10 wherein the leading end and the trailing end of each of the spacers are spaced arcuately between 15 degrees to 180 degrees.

12. The bone stabilizing cabling system of claim 10 wherein the leading end and the trailing end of each of the spacers are spaced arcuately from 90 degrees to 180 degrees.

13. The bone stabilizing cabling system of claim 10 wherein:
each of the spacers further includes a third pair of feet located between the two pairs of feet; and
the feet of the two pairs of feet each have a terminal end face that lies in a plane defined by a respective one of the leading end and the trailing end.

14. The bone stabilizing cabling system of claim 13 wherein the feet of the third pair of feet each have the first shape.

15. The bone stabilizing cabling system of claim 9 further comprises:
a cable, wherein the cable is inserted through the aperture of each of the spacers and when tightened, secures each spacer in contact with the bone securely to reinforce the bone.

16. The bone stabilizing cabling system of claim 15 wherein the feet of the two or more spacers have a width wider than the cable passed through the two or more spacers to increase the contact area of the two or more spacers such that penetration of the two or more spacers and or cortical compromise by the two or more spacers is prevented thereby providing a stable fracture fixation construct.

17. The fracture minimizing cabling system of claim 9 wherein the feet of the first one of the pairs of feet positioned at the leading end of the body of the respective one of the two spacers and the feet of the second one of the pairs of feet positioned at the trailing end of the respective one of the two spacers has the same shape and size.

18. The fracture minimizing cabling system of claim 17 wherein each of the spacers further includes a third pair of feet located between the two pairs of feet.

19. The fracture minimizing cabling system of claim 18 wherein the feet of the third pair of feet each have the first shape.

20. A fracture minimizing cabling system for stabilizing osteoporotic bone comprises:
two or more spacers, wherein each spacer has a longitudinal length and a pair of lateral sides extending along a body of the spacer, the body having an upper portion with an aperture configured to receive a wire or cable and a lower portion having two pairs of feet, wherein the feet of each pair of the two pairs of feet are spaced by a longitudinal gap, wherein the feet of the one or more pairs of feet are each located adjacent to a respective one of the lateral sides of the body and configured to contact osteoporotic bone, wherein a first one of the pairs of feet is positioned at a leading end of the body of a respective one of the two spacers, wherein a second one of the pairs of feet is positioned at a trailing end of the respective one of the two spacers, wherein the two spacers are arranged in an end-to-end manner whereby one of the ends of a first one of the two spacers and one of the ends a second one of the two spacers are abutting each other, wherein adjacent ones of the feet at the abutting ends of the two spacers jointly form a respective one of a full-size foot having a first shape, wherein the full-size foot includes a bone contacting surface having a rounded profile in at least one cross-sectional direction thereof, wherein the bone contacting surface of each of the full-size foot extends partially along a length of the body of a respective one of the spacers, wherein the pairs of the feet and the longitudinal gap are jointly configured to be positioned over an area at risk of a fracture with each foot of a respective one of the pairs of feet positioned on a portion of the osteoporotic bone spaced away from the area at risk of fracture.

21. The fracture minimizing cabling system of claim 20 wherein the longitudinal length of each of the spacers is curved or arcuate.

22. The fracture minimizing cabling system of claim 21 wherein the leading end and the trailing end of each of the spacers are spaced arcuately between 15 degrees to 180 degrees.

23. The fracture minimizing cabling system of claim 21 wherein the leading end and the trailing end of each of the spacers are spaced arcuately from 90 degrees to 180 degrees.

24. The fracture minimizing cabling system of claim 20 wherein:
   each of the spacers further includes a third pair of feet located between the two pairs of feet; and
   the feet of the two pairs of feet each have a terminal end face that lies in a plane defined by a respective one of the leading end and the trailing end.

25. The fracture minimizing cabling system of claim 24 wherein the feet of the third pair of feet each have the first shape.

26. The fracture minimizing cabling system of claim 20 further comprises:
   a cable, wherein the cable is inserted through the aperture of each of the spacers and when tightened, secures each spacer in contact with the osteoporotic bone securely to set and stabilize the osteoporotic bone.

27. The fracture minimizing cabling system of claim 26 wherein the feet of the two or more spacers have a width wider than the cable passed through the two or more spacer to increase the contact area of the two or more spacer such that penetration of the two or more spacers and or cortical compromise by the two or more spacer is prevented thereby providing a stable fracture fixation construct.

28. The fracture minimizing cabling system of claim 20 wherein the feet of the first one of the pairs of feet positioned at the leading end of the body of the respective one of the two spacers and the feet of the second one of the pairs of feet positioned at the trailing end of the respective one of the two spacers has the same shape and size.

29. The fracture minimizing cabling system of claim 28 wherein each of the spacers further includes a third pair of feet located between the two pairs of feet.

30. The fracture minimizing cabling system of claim 29 wherein the feet of the third pair of feet each have the first shape.

* * * * *